(12) United States Patent
Hughett

(10) Patent No.: US 7,052,504 B2
(45) Date of Patent: May 30, 2006

(54) AUTOMATED-FEED SURGICAL CLIP APPLIER AND RELATED METHODS

(75) Inventor: J. David Hughett, Wake Forest, NC (US)

(73) Assignee: Teleflex Incorporated, Limerick, PA (US)

( * ) Notice: Subject to any disclaimer, the term of this patent is extended or adjusted under 35 U.S.C. 154(b) by 306 days.

(21) Appl. No.: 10/299,360

(22) Filed: Nov. 19, 2002

(65) Prior Publication Data

US 2004/0097970 A1    May 20, 2004

(51) Int. Cl.
*A61B 17/10* (2006.01)

(52) U.S. Cl. .................. 606/142; 606/139; 606/143

(58) Field of Classification Search ................ 606/139, 606/142, 143
See application file for complete search history.

(56) References Cited

U.S. PATENT DOCUMENTS

| | | | |
|---|---|---|---|
| 3,270,745 A | 9/1966 | Wood ........................... 128/325 |
| 3,326,216 A | 6/1967 | Wood ........................... 128/325 |
| 3,363,628 A | 1/1968 | Wood ........................... 128/325 |
| 3,439,522 A | 4/1969 | Wood ........................... 72/410 |
| 3,439,523 A | 4/1969 | Wood ........................... 72/410 |
| 4,146,130 A | 3/1979 | Samuels et al. ............. 206/340 |
| 4,509,518 A | 4/1985 | McGarry et al. ............ 128/325 |
| 4,646,740 A | 3/1987 | Peters et al. ................. 128/325 |
| 4,662,555 A | 5/1987 | Thornton ..................... 227/19 |
| 4,834,096 A | 5/1989 | Oh et al. ...................... 128/325 |
| 5,032,127 A * | 7/1991 | Frazee et al. ................ 606/143 |
| 5,035,692 A * | 7/1991 | Lyon et al. .................. 606/143 |
| 5,047,038 A | 9/1991 | Peters et al. ................. 606/139 |
| 5,062,846 A | 11/1991 | Oh et al. ...................... 606/158 |
| 5,100,416 A | 3/1992 | Oh et al. ...................... 606/139 |
| 5,104,395 A | 4/1992 | Thornton et al. ........... 606/143 |
| 5,112,343 A | 5/1992 | Thornton ..................... 606/143 |
| 5,192,288 A * | 3/1993 | Thompson et al. ......... 606/143 |
| 5,282,808 A * | 2/1994 | Kovac et al. ................ 606/143 |
| 5,403,327 A | 4/1995 | Thornton et al. ........... 606/143 |
| 5,509,920 A | 4/1996 | Phillips et al. .............. 606/157 |
| 5,527,320 A | 6/1996 | Carruthers et al. ......... 606/143 |
| 5,634,930 A | 6/1997 | Thornton et al. ........... 606/143 |
| 5,997,552 A * | 12/1999 | Person et al. ................ 606/139 |
| 6,059,799 A * | 5/2000 | Aranyi et al. ............... 606/143 |
| 6,099,537 A * | 8/2000 | Sugai et al. ................. 606/143 |
| 6,673,083 B1 * | 1/2004 | Kayan et al. ................ 606/143 |
| 6,824,547 B1 * | 11/2004 | Wilson et al. .............. 606/143 |

* cited by examiner

*Primary Examiner*—Glenn K. Dawson
*Assistant Examiner*—Darwin P Erezo
(74) *Attorney, Agent, or Firm*—Baker & Hostetler LLP

(57) ABSTRACT

A surgical clip applying apparatus comprises an actuator device, a pair of opposing jaws, and an elongate assembly interposed therebetween. A clip driving device disposed in the elongate assembly is actuated by the actuator device to sequentially drive clips through the elongate assembly into engagement with the jaws. A clip control element is disposed in the elongate assembly at a distal end thereof. The clip control element comprises first, second, and third clip control surfaces. The first clip control surface contacts a first end of a clip to cause the clip to rotate about the first end. The second and third clip control surfaces receive a second end of the clip therebetween prior to the clip being driven into engagement with the jaws. A chicane is provided near the distal end of the elongate assembly to provide a diverting path for clips so that as one clip is being rotated, the next clip can be further advanced without contacting the rotating clip.

14 Claims, 33 Drawing Sheets

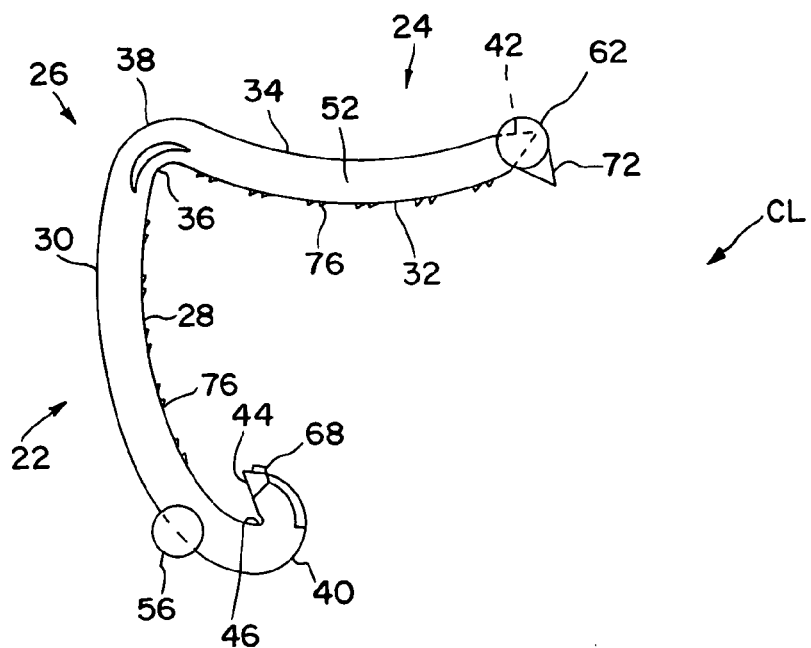
FIG. IA
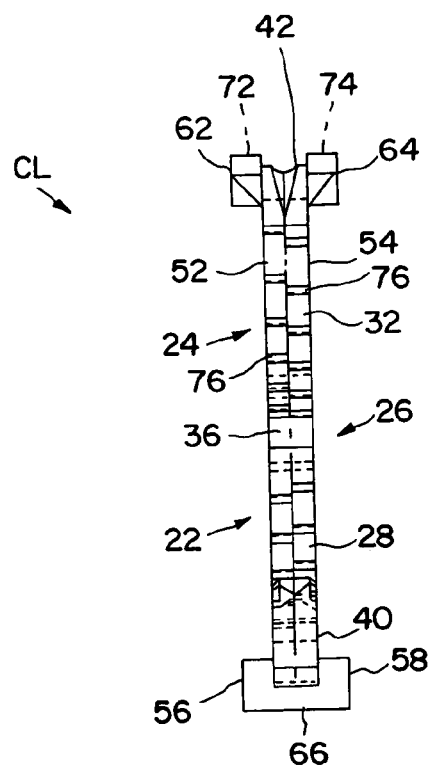
FIG. IB

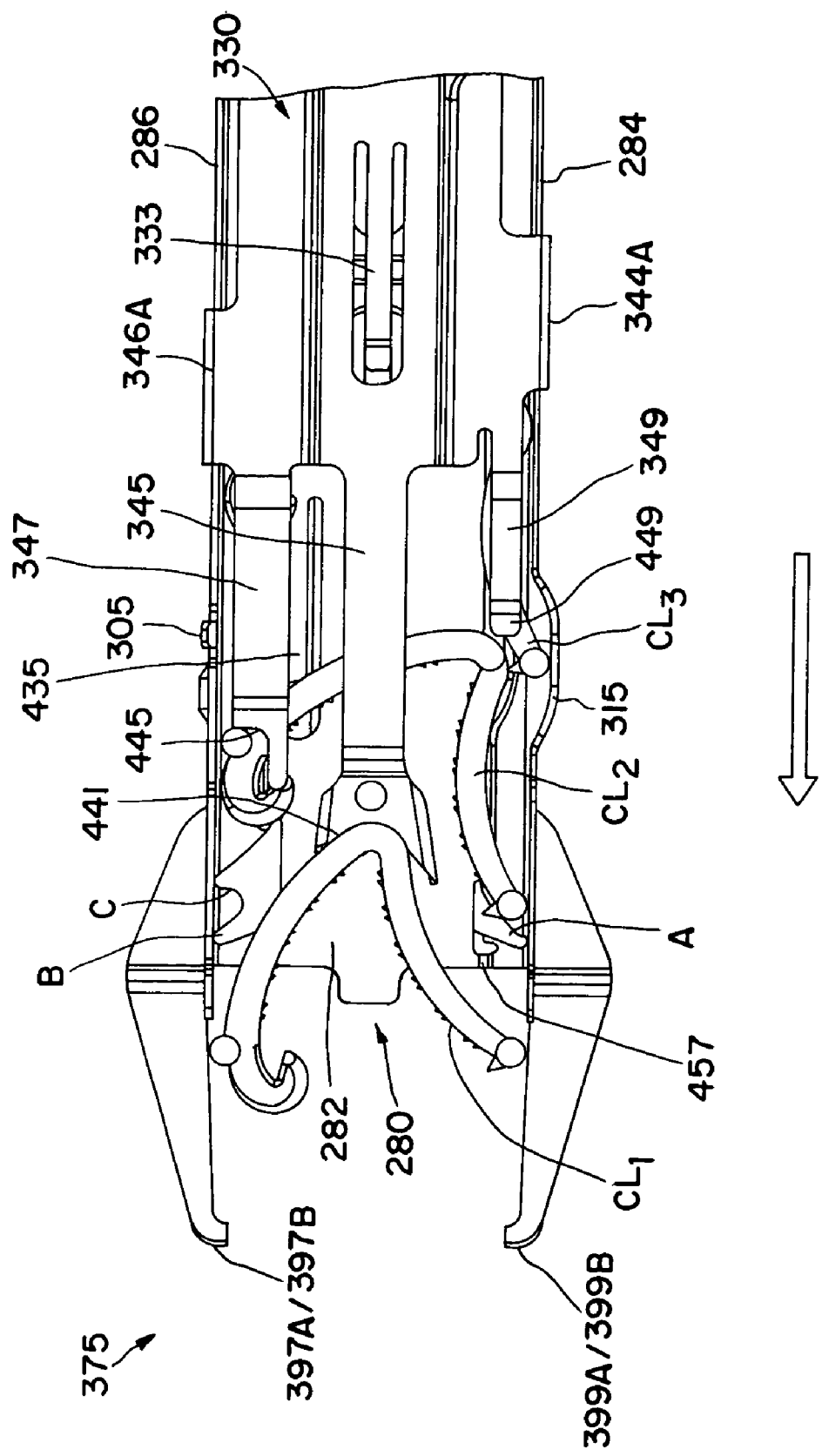
FIG. IIC

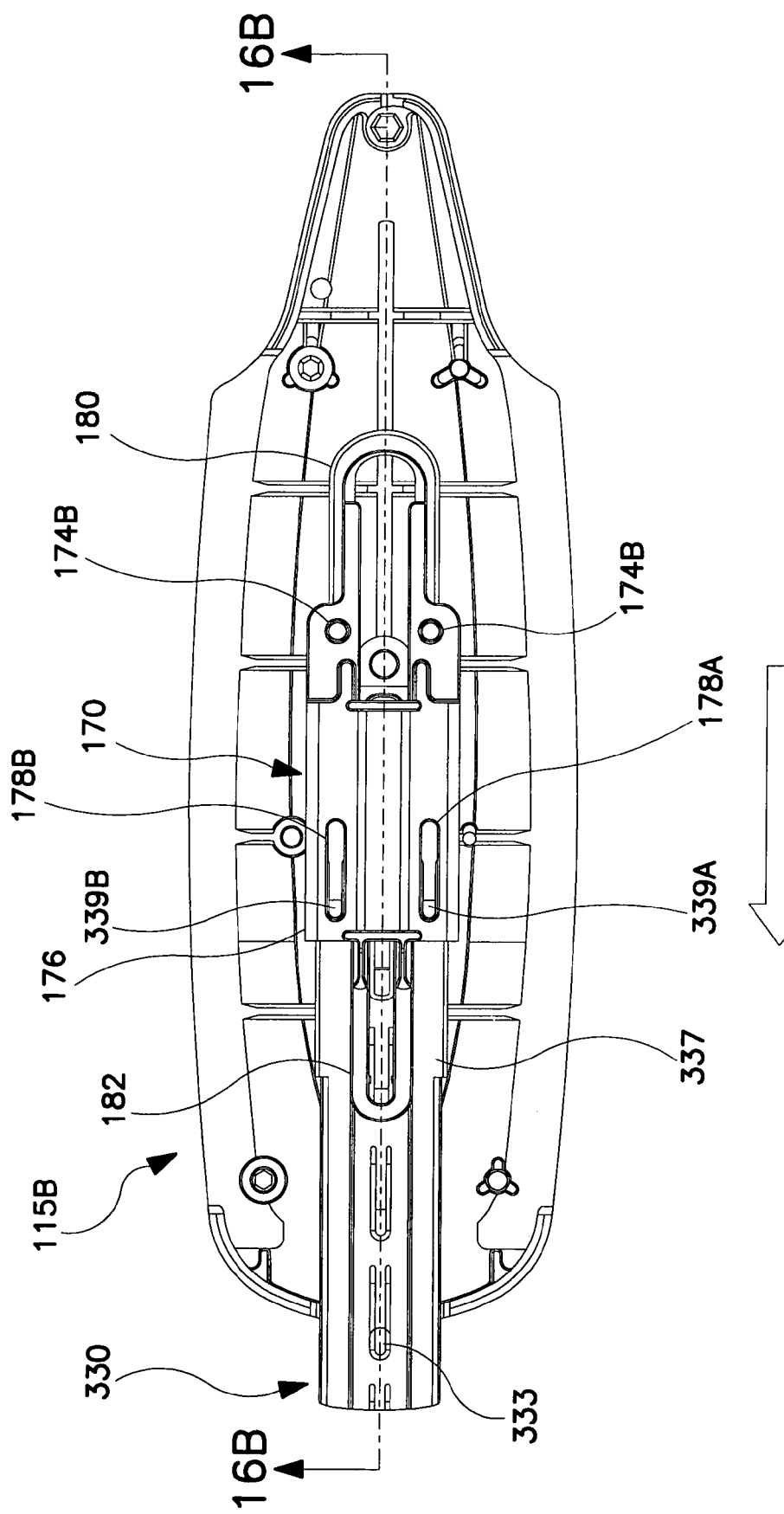

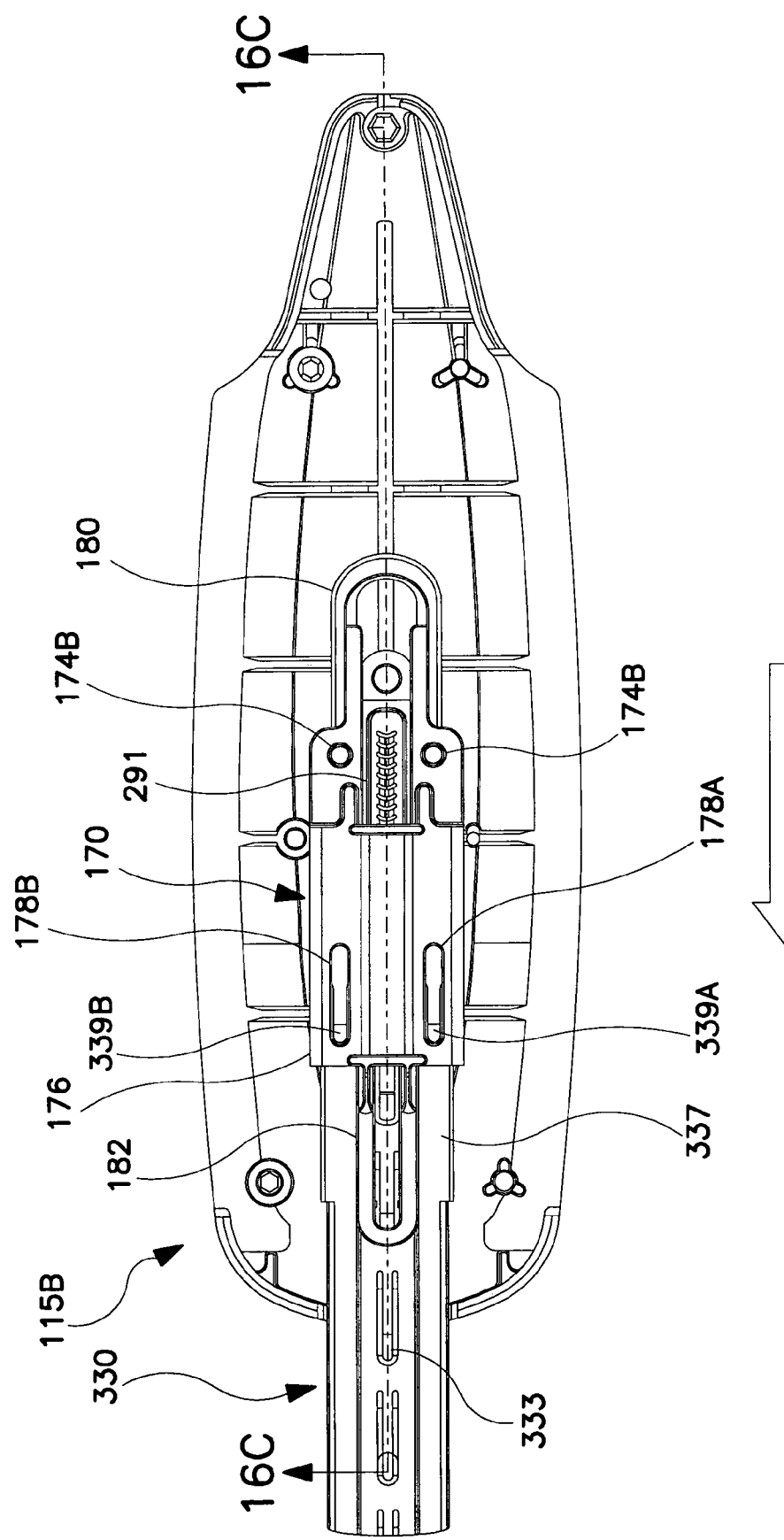

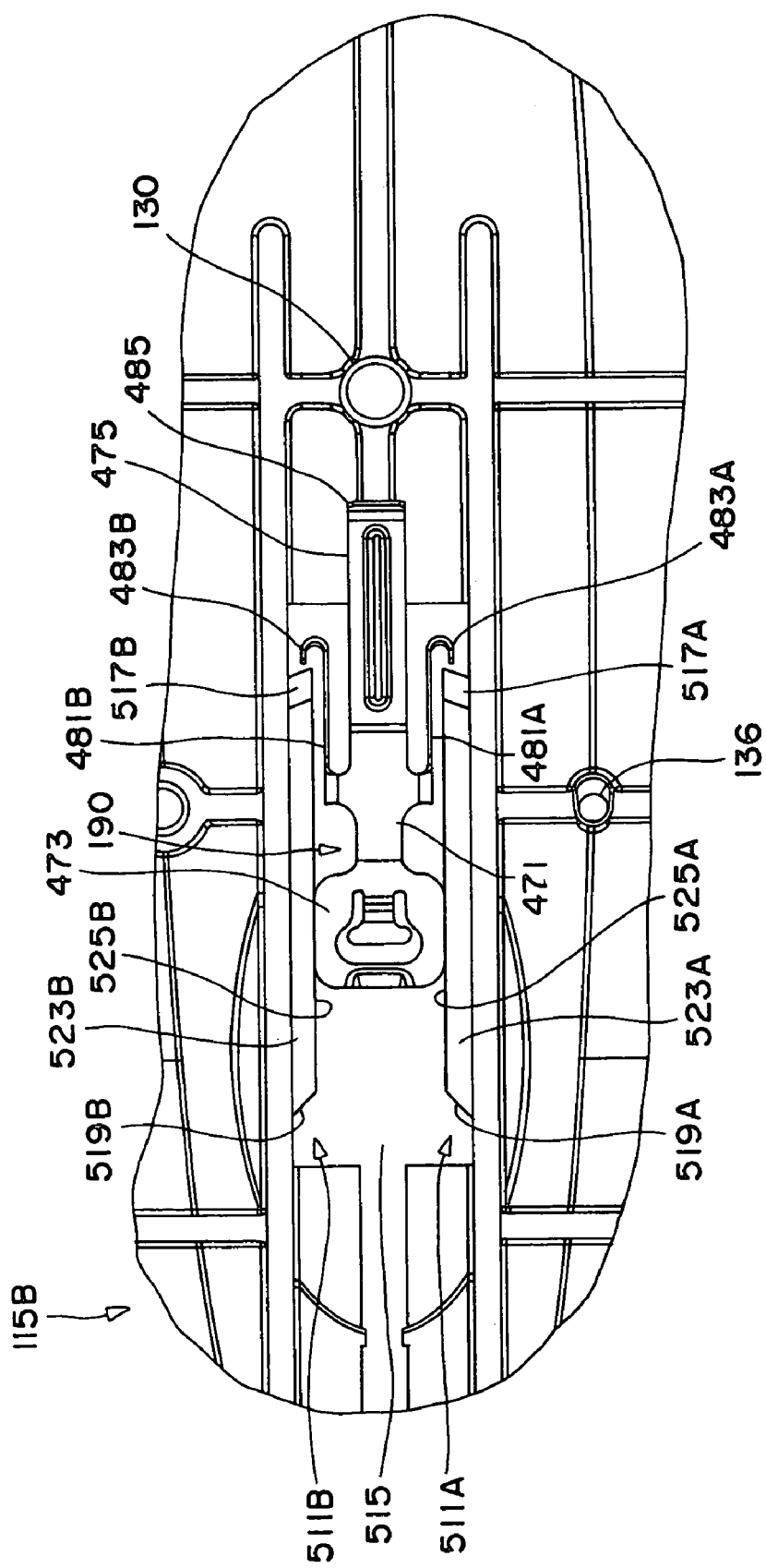

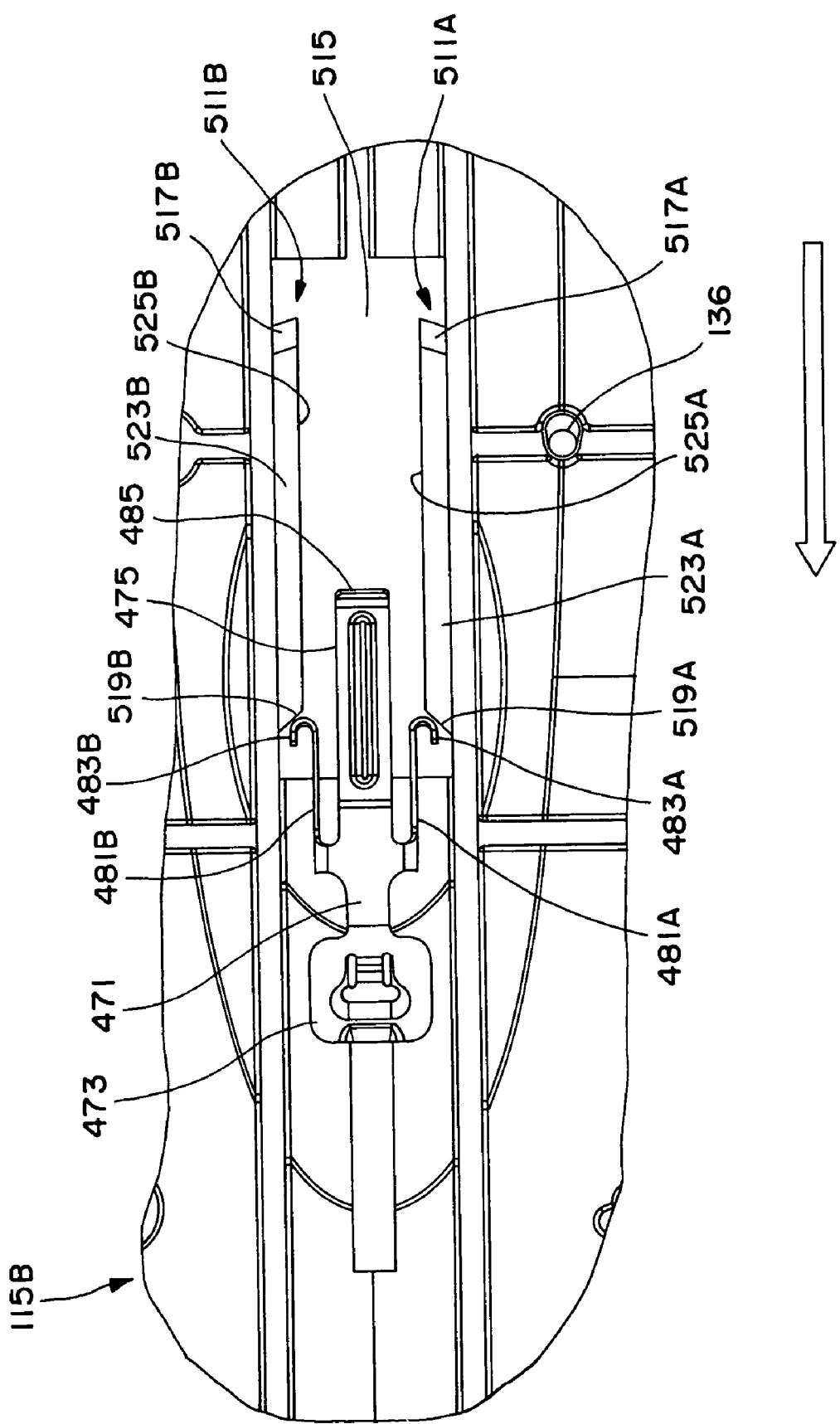

AUTOMATED-FEED SURGICAL CLIP APPLIER AND RELATED METHODS

TECHNICAL FIELD

The present invention generally relates to surgical clip applying instruments and their use in manipulating clips in surgical procedures such as vessel ligation. More particularly, the present invention relates to a clip applier particularly adapted for manipulating polymeric asymmetric clips and sequentially feeding such clips in an automated manner.

BACKGROUND ART

Many surgical procedures require vessels or other tissues of the human body to be ligated during the surgical process. For example, many surgical procedures require cutting blood vessels (e.g., veins or arteries), and these blood vessels may require ligation to reduce bleeding. In some instances, a surgeon may wish to ligate the vessel temporarily to reduce blood flow to the surgical site during the surgical procedure. In other instances a surgeon may wish to permanently ligate a vessel. Ligation of vessels or other tissues can be performed by closing the vessel with a ligating clip, or by suturing the vessel with surgical thread. The use of surgical thread for ligation requires complex manipulations of the needle and suture material to form the knots required to secure the vessel. Such complex manipulations are time-consuming and difficult to perform, particularly in endoscopic surgical procedures that afford limited space and visibility. By contrast, ligating clips are relatively easy and quick to apply. Accordingly, the use of ligating clips in both endoscopic and open surgical procedures has grown dramatically.

Various types of hemostatic and aneurysm clips are used in surgery for ligating blood vessels or other tissues to stop the flow of blood. Such clips have also been used for interrupting or occluding ducts and vessels in particular surgeries such as sterilization procedures. Typically, a clip is applied to the vessel or other tissue by using a dedicated mechanical instrument commonly referred to as a surgical clip applier, ligating clip applier, or hemostatic clip applier. A clip applier designed for use with asymmetric plastic clips in an open (i.e., non-endoscopic) surgical procedure is disclosed in U.S. Pat. No. 5,100,416 to Oh et al., assigned to the assignee of the present invention. The clip applier is used to position the clip over the desired vessel and its jaws are actuated, typically using an actuating mechanism disposed in the handle of the device, to close the clip about the vessel. The clip is typically left permanently in place after application to the tissue. In other cases, at some point after hemostasis or occlusion occurs, the clip can be removed if required by using a separate instrument dedicated for that purpose, i.e., a clip removal instrument.

Ligating clips can be classified according to their geometric configuration (e.g., symmetric clips or asymmetric clips), and according to the material from which they are manufactured (e.g., metal clips or polymeric clips). Symmetric clips are generally "U" or "V" shaped and thus are substantially symmetrical about a central, longitudinal axis extending between the legs of the clip. Symmetric clips are usually constructed from metals such as stainless steel, titanium, tantalum, or alloys thereof. By means of a dedicated clip applier, the metal clip is permanently deformed over the vessel. An example of one such clip is disclosed in U.S. Pat. No. 5,509,920 to Phillips et al. An example of a metallic clip applier is disclosed in U.S. Pat. No. 3,326,216 to Wood, in which a forceps-type applier having conformal jaws is used to grip and maintain alignment of the clip during deformation. Such appliers may additionally dispense a plurality of clips for sequential application, as disclosed in U.S. Pat. No. 4,509,518 to McGarry et al.

With the advent of high technology diagnostic techniques using computer tomography (CATSCAN) and magnetic resonance imaging (MRI), metallic clips have been found to interfere with the imaging techniques. To overcome such interference limitations, biocompatible polymers have been increasingly used for surgical clips. Unlike metallic clips, which are usually symmetric, polymeric clips are usually asymmetric in design and hence lack an axis of symmetry. Inasmuch as the plastic clip cannot be permanently deformed for secure closure around a vessel or other tissue, latching mechanisms have been incorporated into the clip design to establish closure conditions and to secure against re-opening of the vessel. For example, polymeric clips are disclosed in U.S. Pat. No. 4,834,096 to Oh et al. and U.S. Pat. No. 5,062,846 to Oh et al., both of which are assigned to the assignee of the present invention. These plastic clips generally comprise a pair of curved legs joined at their proximal ends with an integral hinge or heel. The distal ends of the curved legs include interlocking latching members. The distal end of one leg terminates in a lip or hook structure into which the distal end of the other leg securely fits to lock the clip in place. The distal ends of the clips taught by Oh et al. also include lateral bosses that are engaged by the jaws of the clip applier.

A clip applier specifically designed for asymmetric plastic clips, such as the aforementioned U.S. Pat. No. 5,100,416 to Oh et al., is used to close the clip around the tissue to be ligated, and to latch or lock the clip in the closed condition. In operation, the jaws of this clip applier are actuated into compressing contact with the legs of the clip. This causes the legs to pivot inwardly about the hinge, thereby deflecting the hook of the one leg to allow reception therein of the distal end of the other leg.

In addition to compatibility with sophisticated diagnostic techniques, asymmetric clips have other advantages over symmetric clips. For example, because asymmetric clips are formed from polymeric materials, the mouths of asymmetric clips can be opened wider than the mouths of symmetric clips. This allows a surgeon to position the clip about the desired vessel with greater accuracy. In addition, a clip of the type described in U.S. Pat. Nos. 4,834,096 and 5,062,846 can be repositioned before locking the clip on the vessel or before removing the clip from the vessel, in a process referred to as "approximating" the clip.

As indicated above, U.S. Pat. No. 5,100,416 to Oh et al. discloses a clip applier designed for use with asymmetric plastic clips in an open (i.e., non-endoscopic) surgical procedure. Other types of clip appliers have been developed for applying metallic clips. Clip appliers can also be classified according to whether they are designed for either open surgical procedures or endoscopic surgical procedures. Clip appliers designed for use with metallic clips in open surgery are disclosed in U.S. Pat. No. 3,270,745 to Wood; U.S. Pat. No. 3,326,216 to Wood; U.S. Pat. No. 3,439,522 to Wood; U.S. Pat. No. 3,439,523 to Wood; U.S. Pat. No. 4,146,130 to Samuels et al.; U.S. Pat. No. 4,646,740 to Peters et al. (assigned to the assignee of the present invention); U.S. Pat. No. 4,509,518 to McGarry et al.; U.S. Pat. No. 5,047,038 to Peters et al. (assigned to the assignee of the present invention); and U.S. Pat. No. 5,104,395 to Thornton et al. (assigned to the assignee of the present invention). Clip appliers designed for use with metallic clips in endoscopic surgery are disclosed in U.S. Pat. No. 5,403,327 to Thornton et al.; U.S. Pat. No. 5,112,343 to Thornton; U.S. Pat. No. 5,527,320 to Carruthers et al.; and U.S. Pat. No. 5,634,930 to Thornton et al., all of which are assigned to the assignee of the present invention.

Clip appliers can be further classified according to whether they are manual or automatic. The term "automatic" denotes the kind of clip appliers designed to retain a plurality of hemostatic clips in proximal relation to the jaws of a clip applier. A new clip is automatically fed to the jaws after the previous clip has been crimped or latched into place. Automatic clip appliers are disclosed in the aforementioned U.S. Pat. Nos. 4,509,518; 4,646,740; 5,047,038; 5,104,395; 5,112,343; 5,403,327; 5,527,320; and 5,634,930.

By contrast, the term "manual" denotes the kind of clip appliers that receive one clip at a time between the jaws, and which must be reloaded manually after the previous clip has been crimped or latched. These manual instruments usually have a forceps-type design. The reloading operation is generally accomplished by inserting the jaws of the applier into a clip holder or cartridge that is a physically separate component from the clip applier itself. Many types of clip cartridges currently available contain a plurality of longitudinally-spaced clip-retaining chambers. A single clip is retained in each chamber by a variety of means, and is removed from its chamber by inserting the jaws of the clip applier into the selected clip chamber to engage or grasp the clip sufficiently to overcome whatever clip retention means is utilized, thereby enabling the clip to be removed from the clip chamber. Manual clip appliers are disclosed in the aforementioned U.S. Pat. Nos. 3,270,745; 3,326,216; 3,439,522; 3,439,523; 4,146,130; and 5,100,416.

Conventional clip appliers of all types discussed above typically include a pair of jaws, and a handle or grip assembly designed for manipulation by the hand and fingers of the user to actuate the jaws. In addition, an elongate (e.g., 11 inches) intermediate section separates the jaws and the handle assembly. This intermediate section is usually a shaft section in the case of automatic and/or endoscopic clip appliers, or a pair of pivoting arms in the case of most manual clip appliers. In the case of most automated and/or endoscopic clip appliers, some type of linkage is provided in the shaft section and/or the handle assembly through which the force imparted by the surgeon's hand to move the handles (e.g., squeezing) is transferred into pivoting of the jaws and thus compression of the clip.

A typical automated clip applier is operated by executing a forward stroke and a subsequent return stroke. The forward stroke loads a clip into the jaws of the clip applier and applies the clip to a target vessel or other tissue at the surgical site. The return stroke resets the clip applier for subsequent manipulation of the next available clip stored within the instrument. The forward stroke is executed by squeezing the handles of the instrument to actuate various components thereof. The return stroke is executed by releasing hand pressure on the handles to cause certain components to return to a starting position. At some point during either the forward stroke or the return stroke, the several clips typically stored in the shaft section of the instrument must be advanced toward the jaws in preparation for loading the next available clip into the jaws. The successful operation of such automated clip appliers necessarily requires the use of moving and often reciprocating components, many of which must interact with each other and/or with the clips. Moreover, the moving components must carry out their respective functions without interfering with the advancement and alignment of the clips through the shaft section and the sequential loading of the clips into the jaws, and without failing during a surgical procedure. Accordingly, it is well recognized among persons skilled in the art that a continuing need exists for improvements in the design and operation of automated-feed clip appliers.

DISCLOSURE OF THE INVENTION

In general terms, the present invention provides an automated-feed clip applying instrument that is advantageously employed to manipulate surgical clips such as ligating clips, and especially polymeric, latchable clips of asymmetric design such as those described herein by way of example. Clip appliers provided according to embodiments of the present invention comprise an actuating section, a jaw section, and an elongate section between the actuating and jaw sections. Clips are stored in the elongate section and advanced along the length thereof in response to actuating events caused by operation of the actuating section by the user. The elongate section is designed to store the clips in a serial arrangement, and in a manner that keeps the clips stabilized as they are advanced in an indexing fashion towards the jaw section. As described in more detail below, certain features of the invention allow the clips to be stacked closer together than heretofore possible, thereby permitting a shorter elongate section to be employed. Moreover, the invention provides a clip control system that enables a unique clip loading preparation sequence, in which each clip is advanced toward a distal end of the elongate section and rotated to a position optimal for subsequently loading the clip into the jaw section.

In another aspect, the invention provides a stroke control system that enhances the user's control over the clip applier as well as over a clip loaded in its jaw section, and improves the user's ability to approximate the clip prior to latching the clip to a target tissue. The stroke control system enables the forward stroke of the clip applier to be executed in two separate stages. Both stages are fully controllable by the user through manipulation of the actuating section. During the first stage, all clips stored in the elongate section are advanced along its length, the most distal clip is loaded into the jaw section, and other clips immediately following the most distal clip are prepared for controlled loading into the jaw section in anticipation of subsequent clip applications. During the second stage, the user can repeatedly actuate the jaw section to partially compress and reposition the clip loaded in the jaw section until that clip is ready to be applied. The invention enables such adjustment or approximation of the clip to be accomplished without applying the clip, and without advancing other clips through the elongate section or loading other clips into the jaw section. Once the user determines that the clip loaded in the jaw section is ready to be applied, the user completes the second stage of the forward stroke by operating the actuating section to fully actuate the jaw section. The return stroke is then executed without affecting the remaining clips stored in the clip applier.

According to one embodiment of the present invention, an apparatus for applying surgical clips comprises first and second opposing jaw members, an elongate assembly, a clip driving device, and a clip pivot surface. The first and second jaw members communicate with the actuator device, and are movable to a closed position from an open position in response to actuation by the actuator device. The elongate assembly comprises a proximal end attached to the actuator device and an opposing distal end. The elongate assembly is adapted for containing a serial arrangement of clips between the proximal and distal ends. The clip driving device is disposed in the elongate assembly and communicates with the actuator device. The clip driving device is adapted for sequentially driving clips through the elongate assembly into engagement with the first and second jaw members in response to actuation by the actuator device. The clip pivot surface is disposed in the elongate assembly at its distal end. The clip pivot surface is adapted for contacting a first end of a clip to cause the clip to rotate about the first clip end prior to the clip being driven into engagement with the first and second jaw members.

According to another embodiment of the present invention, an apparatus for applying surgical clips comprises an actuator device, first and second opposing jaw members, an elongate assembly, a clip driving device, and a clip control element. The clip control element is disposed in the elongate assembly at its distal end, and comprises a first clip control surface, a second clip control surface, and a third clip control surface. The first clip control surface is adapted for contacting a first end of a clip to cause the clip to rotate about the first end. The second and third clip control surfaces are adapted for receiving a second end of the clip therebetween prior to the clip being driven into engagement with the first and second jaw members.

Preferably, the elongate assembly comprises a channel member for guiding clips towards the distal end, and the clip driving device moves in relation to the channel member. The clip control element is attached to the channel member.

According to another aspect of this embodiment, the apparatus comprises a fourth clip control surface disposed in the elongate assembly. The fourth clip control surface is adapted to contact the clip while the first clip control surface contacts the first clip end and the second and third clip control surfaces engage the second clip end. Preferably, the fourth clip control surface extends from the channel member when so provided in the elongate assembly.

According to yet another embodiment of the present invention, an apparatus for applying surgical clips comprises an actuator device, first and second opposing jaw members, a channel member, and a clip feeder device. The first and second jaw members communicate with the actuator device, and are movable to a closed position from an open position in response to actuation by the actuator device. The channel member is adapted for containing a serial arrangement of clips along a longitudinal axis thereof. The channel member comprises a proximal channel end attached to the actuator device, an opposing distal channel end, and a base wall extending between the proximal and distal channel ends. The clip feeder device communicates with the actuator device and is axially movable in relation to the channel member. The clip feeder device comprises a clip driving tab extending from a distal feeder end thereof, and a clip rotating tab extending from the distal feeder end. The clip driving tab sequentially drives clips from the channel member into engagement with the first and second jaw members in response to actuation by the actuator device. The clip rotating tab rotates a clip prior to the clip being driven by the clip driving tab.

According to another aspect of this embodiment, the clip feeder device comprises a clip hold-down tab extending from the distal feeder end. The clip hold-down tab biases clips towards the base wall of the channel member.

According to still another embodiment of the present invention, an apparatus for applying surgical clips comprises an actuator device, first and second opposing jaw members, a channel member, and a clip driving device. The channel member is adapted for containing a serial arrangement of clips along a longitudinal axis thereof. The channel member comprises a proximal end attached to the actuator device, an opposing distal end, and a base wall extending between the proximal and distal ends. The base wall comprises a first track and a second track. The first track guides a first side of a clip towards the distal end, and the second track guides a second side of the clip towards the distal end. The first track comprises a main section that is spaced from the second track by a track distance. The first track also comprises a chicane section that is spaced from the second track at a greater distance than the track distance. The chicane section defines a diverting path for the second side of the clip.

According to one aspect of this embodiment, the channel member comprises first and second spaced apart side walls extending substantially perpendicularly from the base wall. The base wall comprises first and second spaced apart axial ribs. The first axial rib and the first side wall cooperatively define the first track. The second axial rib and the second side wall cooperatively define the second track. The first side wall comprises a diverting section extending transversely outwardly in relation to the longitudinal axis. The diverting section and adjacent portion of the first axial rib cooperatively define the chicane section of the first track.

The present invention also provides a method for operating a surgical clip applier, comprising the following steps. A clip applier is provided which comprises first and second opposing jaw members, an actuator device communicating with the jaw members, and an elongate assembly interconnecting the jaw members and the actuator device. A plurality of clips are stored in a serial arrangement along a length of the elongate assembly. Each clip is of the type that comprises a first leg terminating at a first end region, a second leg terminating at a second end region, and a hinge joining the first and second legs. The actuator device is operated to cause at least one of the clips residing in a distal region of the elongate assembly to rotate about the first end region of the at least one clip. This in turn causes the hinge of the at least one clip to move toward a central region within the distal region. While the hinge of the at least one clip is in the central region, the actuator device is operated to drive the at least one clip from the distal region into engagement with the jaw members.

According to one aspect of this method, while the at least one clip is rotating, the first end region of a succeeding clip proximal to the at least one clip is caused to follow a diverted path away from the central region of the distal region of the elongate assembly. This allows the first end region of the succeeding clip to avoid contacting the hinge of the at least one clip while that hinge moves toward the central region within the distal region of the elongate assembly.

It is therefore an object of the present invention to provide a surgical clip applying instrument capable of storing a plurality of clips and sequentially feeding the clips to its jaws in an automated manner.

It is another object of the present invention to provide a clip applying instrument adapted for manipulating surgical clips of the polymeric, asymmetric design.

It is yet another object of the present invention to provide a surgical clip applying instrument adapted for storing the clips in a shorter stack than heretofore possible.

It is still another object of the present invention to provide a surgical clip applying instrument characterized by a clip control system that sequentially prepares and loads clips into its jaws in an optimal, controlled manner.

It is an additional object of the present invention to provide a surgical clip applying instrument that provides a stroke control system that affords the user more control over the instruments and the clips manipulated thereby as compared to conventional instruments.

Some of the objects of the invention having been stated hereinabove, and which are addressed in whole or in part by the present invention, other objects will become evident as the description proceeds when taken in connection with the accompanying drawings as best described hereinbelow.

BRIEF DESCRIPTION OF THE DRAWINGS

FIG. 1A is a side elevation view of one example of an asymmetric surgical clip suitable for use in conjunction with the clip applier of the present invention;

FIG. 1B is a front elevation view of the surgical clip illustrated in FIG. 1A directed into the open side of the clip;

FIGS. 11A–11E are sequential, side elevation views of the interior of the distal end of the channel assembly of the clip applier, illustrating the operations performed on clips stored within the clip applier in preparation for sequentially applying such clips at a surgical site;

FIGS. 14A–14E are sequential, top plan views of the interior of the actuator assembly of the clip applier, illustrating the movement of the coupling in relation to a ratcheting mechanism provided in accordance with the present invention;

FIGS. 15A–15E are sequential, top plan views of the interior of the actuator assembly of the clip applier, illustrating the movement of the anti-backup spring element in relation to cam surfaces formed in the structure of the actuator assembly.

DETAILED DESCRIPTION OF THE INVENTION

Figure 2:
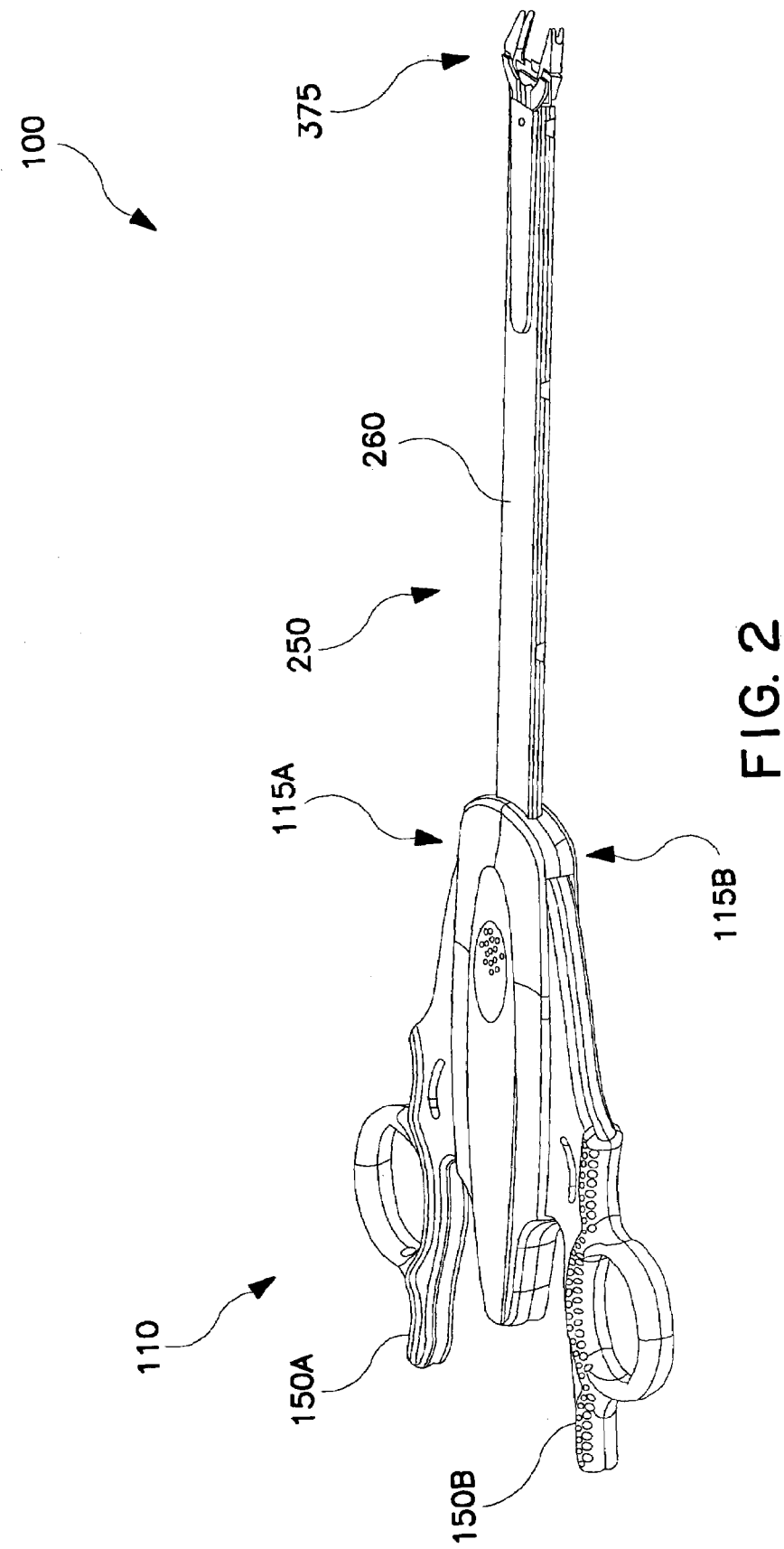
FIG. 2 is a perspective view of a clip applier of the present invention shown with its actuator and jaw assemblies in an open position.

The clip applier of the present invention as described in detail below is particularly designed for use in manipulating a polymeric, asymmetric clip that is movable into a closed, latched state when clamped onto tissue. An example of this type of clip, generally designated CL, is illustrated in FIGS. 1A and 1B. Clip CL preferably comprises a one-piece integral polymeric body formed from a suitable strong, biocompatible engineering plastic such as the type commonly used for surgical implants. Examples include polyethylene terephthalate (PET), polybutylene terephthalate (PBT), polyoxymethylene, or other thermoplastic materials having similar properties that can be injection-molded, extruded or otherwise processed into like articles.

The body of clip CL comprises a first or outer leg, generally designated 22, and a second or inner leg, generally designated 24. First and second legs 22 and 24 are joined at their proximal ends by an integral hinge or heel section, generally designated 26. First and second legs 22 and 24 have complementary arcuate profiles. Thus, first leg 22 has a concave inner surface 28 and a convex outer surface 30, and second leg 24 has a convex inner surface 32 and a concave outer surface 34. Convex inner surface 32 of second leg 24 and concave inner surface 28 of first leg 22 have substantially matching radii of curvature. Hinge section 26 has a concave inner surface 36 and a convex outer surface 38. Concave inner surface 36 of hinge section 26 integrally joins concave inner surface 28 of first leg 22 and convex inner surface 32 of second leg 24. Convex outer surface 38 of hinge section 26 integrally joins convex outer surface 30 of first leg 22 and concave outer surface 34 of second leg 24. First leg 22 transitions to a curved, C-shaped hook section 40 at its distal end. Second leg 24 transitions to a pointed tip section 42 at its distal end. Hook section 40 at its distal end curves inwardly back toward concave inner surface 28 of first leg 22, and has a transverse beveled surface 44. Beveled surface 44 and concave inner surface 28 define a latching recess 46, which is adapted for conformally engaging tip section 42 in the course of compressing clip CL into a latched or locked position around a vessel or other tissue.

As best shown in FIG. 1B, which is an elevation view directed into the open concave side of clip CL, clip CL comprises parallel, opposed side surfaces 52 and 54. Typically, the body of clip CL has a constant thickness between side surfaces 52 and 54. Adjacent to the distal end of the first leg 22 and immediately inwardly of hook section 40, a pair of cylindrical bosses 56 and 58 are formed coaxially on the opposed lateral surfaces of first leg 22. In the illustrated example of clip CL, a bridge section 66 couples bosses 56 and 58 together. As evident in FIG. 1A, bosses 56 and 58 project outwardly beyond convex outer surface 30 of first leg 22. Referring back to FIG. 1B, at the distal end of inner leg 24, another pair of cylindrical bosses 62 and 64 are formed coaxially on the opposed lateral surfaces of inner leg 24 at tip section 42. As evident in FIG. 1A, bosses 62 and 64 of second leg 24 extend longitudinally forwardly beyond tip section 42. Also in the illustrated example of clip CL, hook section 40 of first leg 22 terminates at a sharp tip 68, the distal end of second leg 24 includes a pair of sharp tissue-penetrating teeth 72 and 74, and both first and second legs 22 and 24 have a plurality of protrusions or teeth 76 extending from their respective inner surfaces 28 and 32. These latter features are designed to engage the tissue of the vessel being clamped and assist in preventing the vessel from sliding laterally or longitudinally during or following clip closure. It will be noted, however, that other clips equally suitable for use in conjunction with the invention do not necessarily contain such features.

In the practice of ligating a vessel as understood by persons skilled in the art, clip CL is designed to be compressed into a latched or locked position around the vessel through the use of an appropriate clip applicator instrument, such as the known type described in the aforementioned U.S. Pat. No. 5,100,416, or the novel clip applying instrument described and claimed herein. Typically, the clip applicator instrument engages bosses 56, 58, 62 and 64 of clip CL and pivots bosses 56, 58, 62 and 64 inwardly about hinge section 26. This causes first and second legs 22 and 24 to close around the vessel, with convex inner surface 32 of second leg 24 and complementary concave inner surface 28 of first leg 22 contacting the outer wall of the vessel. Tip section 42 of second leg 24 then begins to contact hook section 40. Further pivotal movement by the clip applicator instrument longitudinally elongates first leg 22 and deflects hook section 40 outwardly, allowing tip section 42 to align with and engage latching recess 46. Upon release of the clip applicator instrument, tip section 42 snaps into and is conformably seated in latching recess 46, at which point clip CL is in its latched condition. In the latched condition, tip section 42 is engaged between concave inner surface 28 of first leg 22 and beveled surface 44 of hook section 40, thereby securely clamping a designated vessel or other tissue between concave inner surface 28 of first leg 28 and convex inner surface 32 of second leg 24.

Clips similar to clip CL are described in detail in commonly assigned U.S. Pat. No. 4,834,096 to Oh et al. and U.S. Pat. No. 5,062,846 to Oh et al., the disclosures of which are incorporated herein in their entireties. In addition, a particularly suitable clip is the HEM-O-LOK® clip commercially available from the assignee of the present invention. These clips are currently available in sizes designated "M", "ML", and "L". The clip applier of the invention described hereinbelow can be dimensioned to specifically handle any sizes of HEM-O-LOK® clips commercially available.

It will be understood that surgical clips such as clip CL just described are intended to represent illustrative examples of the types of clips compatible with the clip applier of the invention described herein, and thus do not limit the invention. In general terms, clips suitable for use in connection with the present invention comprise asymmetric bodies having two legs joined at a hinge section about which the two legs can pivot toward and away from each other. The distal ends of the legs are structured so as to enable one leg to become removably engaged with the other leg in response to compression of the clip between the jaws of the clip applier. Preferably, the legs have bosses, pins or other suitable features designed to improve the manipulation of the legs by the jaws of the clip applier. For the purposes of describing the clip applier of the present invention below, clip CL illustrated in FIGS. 1A and 1B is referred to for convenience and is characterized as having a hook side and a double-tooth side. Referring to FIGS. 1A and 1B, the hook side corresponds to first leg 22 containing hook section 40, and the double-tooth side corresponds to second leg 24 containing the pair of sharp tissue-penetrating teeth 72 and 74.

Figure 3:
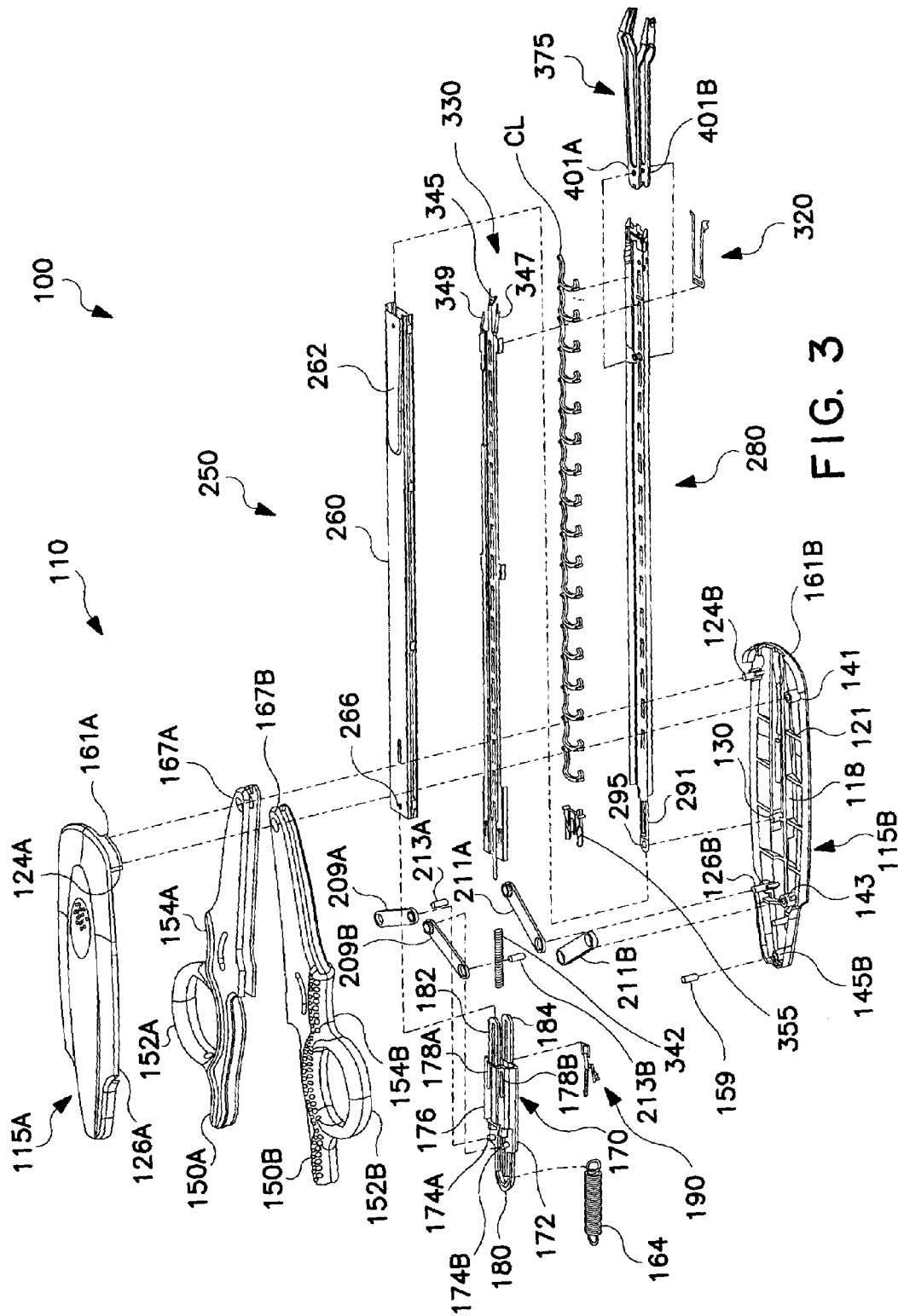
FIG. 3 is an exploded view of the clip applier illustrated in FIG. 2.
Figure 4:
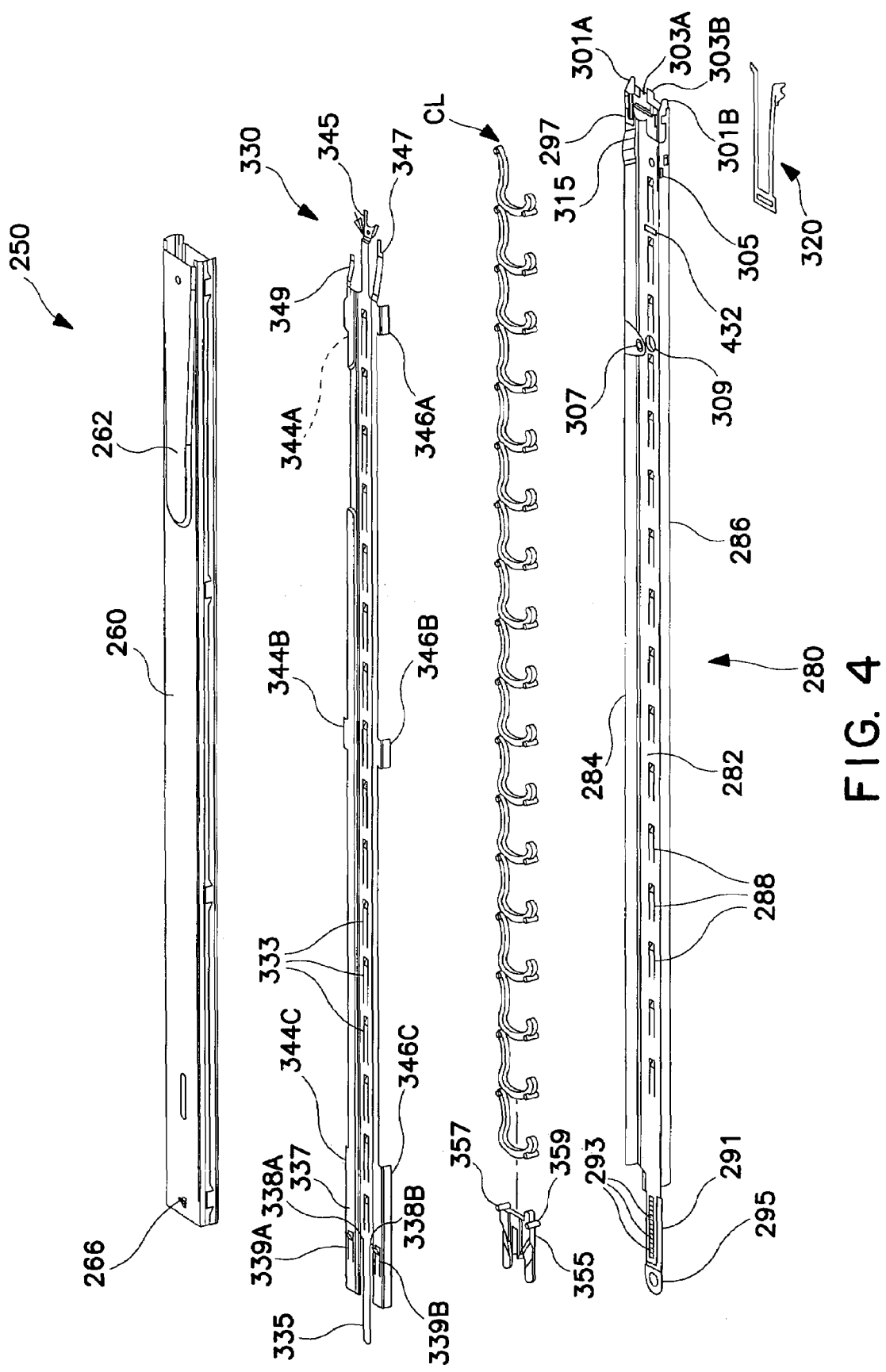
FIG. 4 is an exploded view showing the details of a channel assembly provided with the clip applier.
Figure 5:
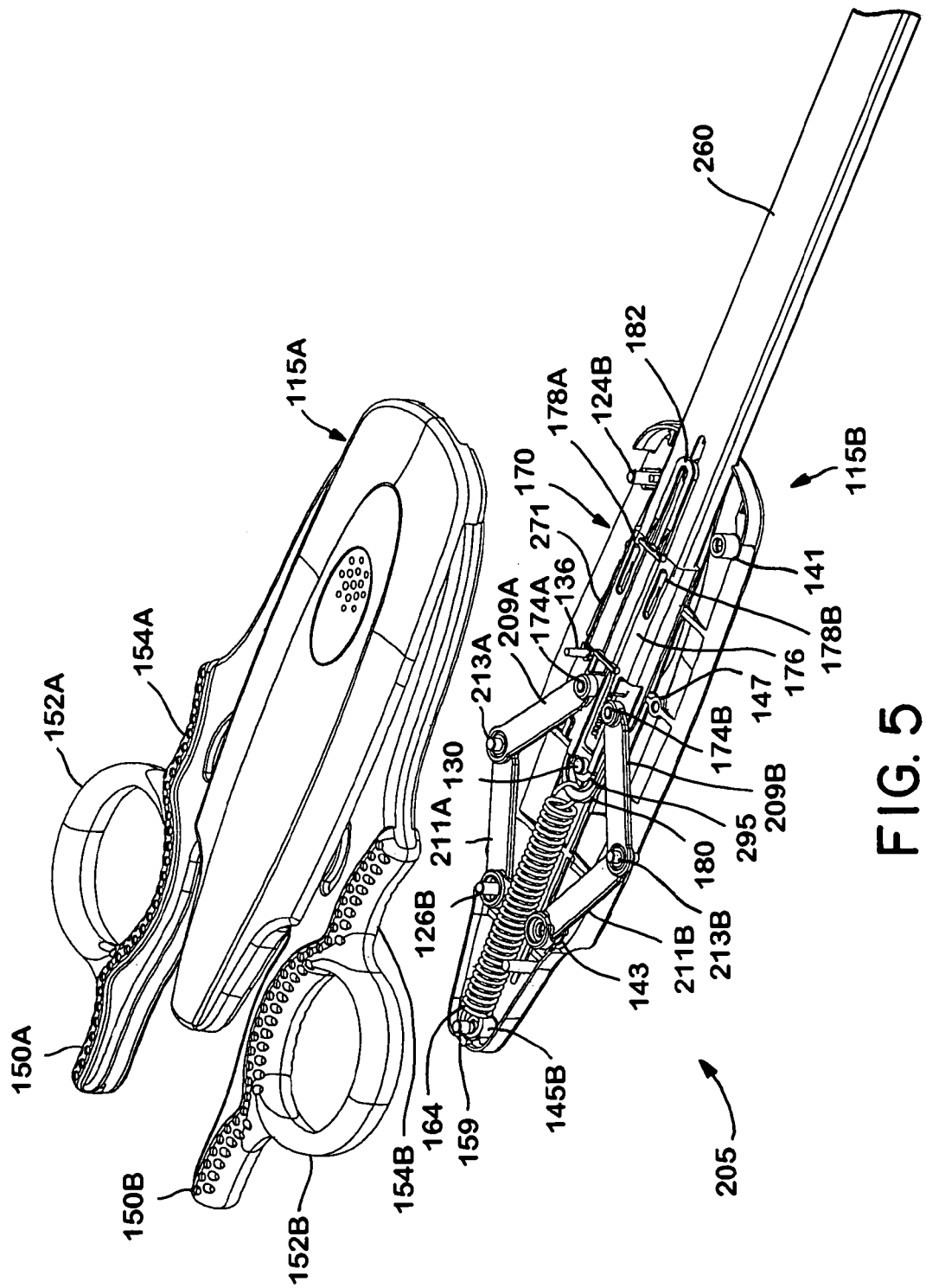
FIG. 5 is a perspective, partially assembled view of the actuator assembly provided with the clip applier.

Referring now to FIGS. 2–5, an automated-feed surgical clip applier, generally designated 100, is illustrated in accordance with an exemplary, preferred embodiment of the present invention. FIG. 2 illustrates clip applier 100 in its assembled condition, FIGS. 3 and 4 illustrate unassembled conditions, and FIG. 5 illustrates a partially assembled condition. In the preferred embodiment, as particularly shown in FIG. 2, clip applier 100 generally comprises an actuator assembly, generally designated 110; an elongate channel assembly, generally designated 250; and a jaw assembly, generally designated 375. Clip applier 100 is particularly designed to handle polymeric, asymmetric surgical clips of the type described above, such as clip CL illustrated in FIGS. 1A and 1B. Actuator assembly 110 is designed to be manipulated by the user of clip applier 100 to actuate jaw assembly 375 and a clip feeding mechanism described below, through the interaction of mechanical components associated with actuator assembly 110 and channel assembly 250 as described in detail below. Channel assembly 250 is designed to store a number of clips CL in series (see FIGS. 3 and 4), to convey clips CL incrementally along the length of channel assembly 250, and to load clips CL one-by-one into jaw assembly 375 in preparation for application at a surgical site. Although seventeen clips CL are illustrated in FIGS. 3 and 4, it will be understood that channel assembly 250 could be designed to handle more or less clips CL. Jaw assembly 375 is designed to manipulate and compress clips CL as described above.

Referring to FIG. 3, the primary structural components of actuator assembly 110 include a housing and a trigger assembly, both of which preferably are constructed from molded plastic components. The housing has a two-piece configuration comprising a first shroud, generally designated 115A, and a second shroud, generally designated 115B. In a conventional manner and as illustrated in FIG. 3, first and second shrouds 115A and 115B each include a number of molded axial ribs 118 and transverse ribs 121. Axial and transverse ribs 118 and 121 are provided for structural integrity and spacing, and/or for alignment and mounting of certain components enclosed by first and second shrouds 115A and 115B. As illustrated in FIGS. 3, 5, 6A and 6B, first and second shrouds 115A and 115B also comprise molded features such as posts 124A, 124B, 126A, 126B, 130 and 136 and blind bores 141, 143, 145A, 145B and 147, which assist in aligning and assembling first and second shrouds 115A and 115B together and/or mounting other components of clip applier 100 to actuator assembly 110.

Figure 6A:
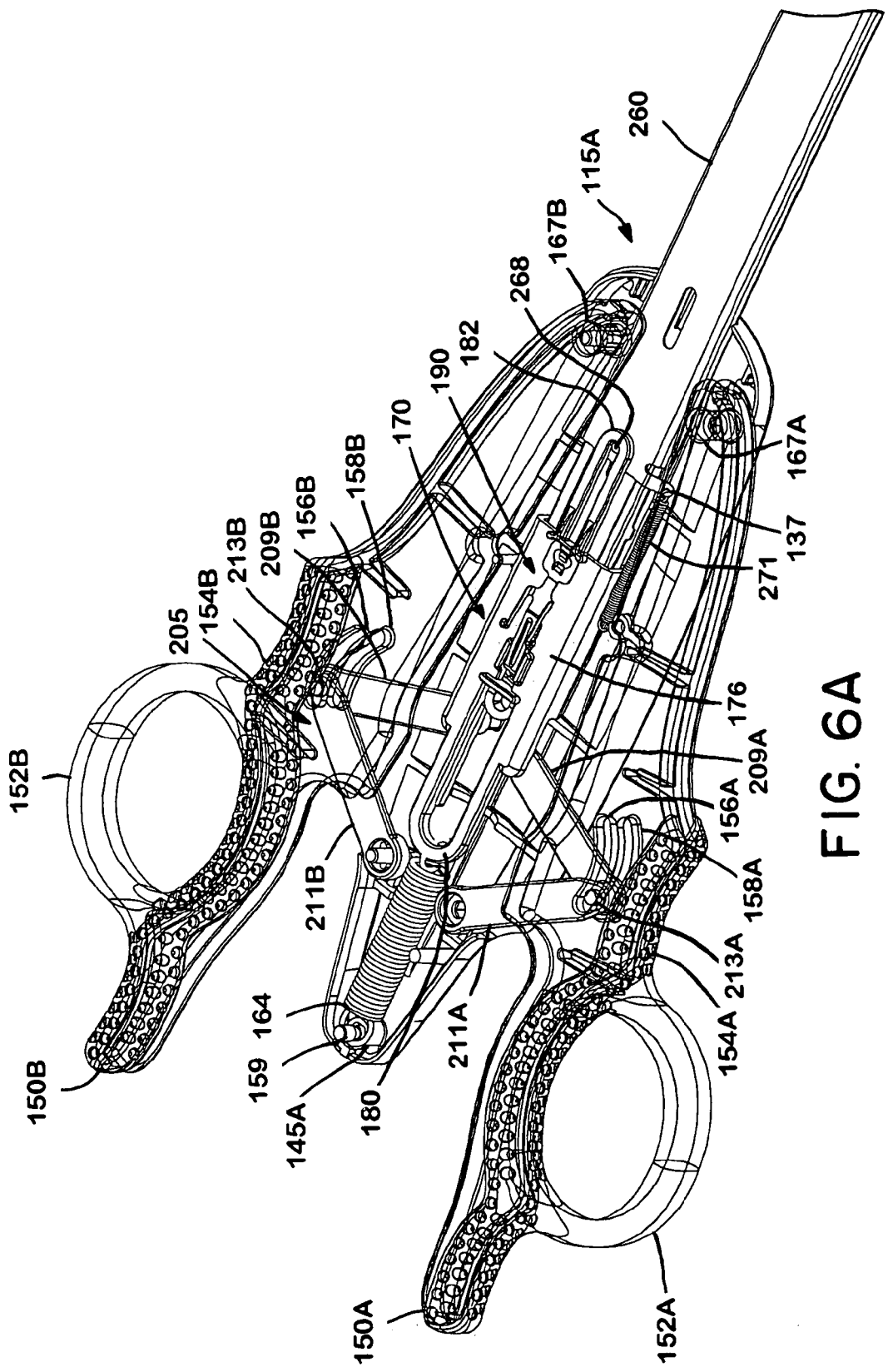
FIG. 6A is a detailed perspective view of the actuator assembly of the clip applier shown in an open position.
Figure 6B:
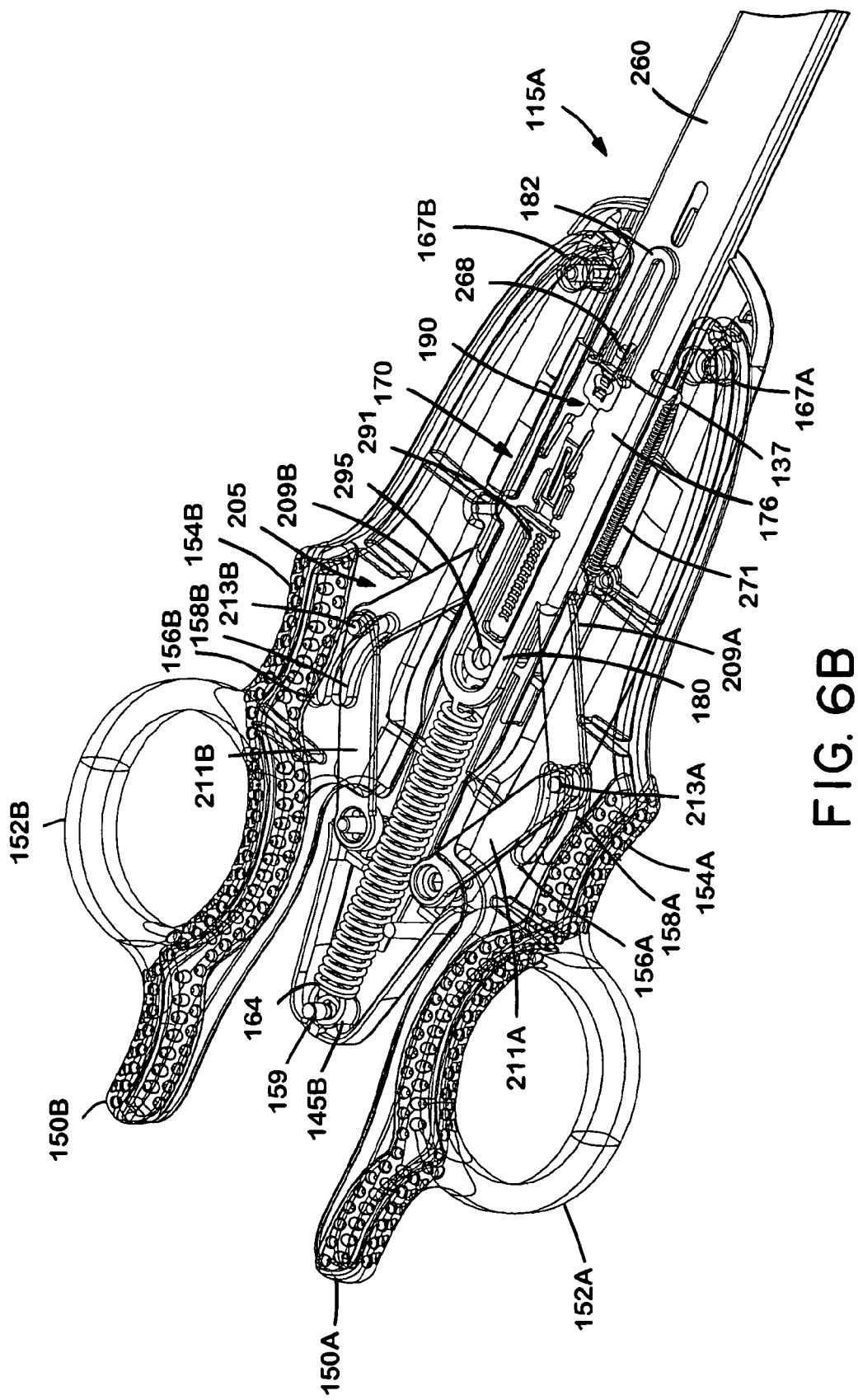
FIG. 6B is a detailed perspective view of the actuator assembly of the clip applier shown in a closed position.

Referring to FIGS. 3, 6A and 6B, the trigger assembly comprises a first trigger 150A and a second trigger 150B. In a conventional manner and as illustrated in FIG. 3, first and second triggers 150A and 150B include structural features, such as loops 152A and 152B and contoured surfaces 154A and 154B, to facilitate their manipulation by the hand of the user. First and second triggers 150A and 150B are pivotable between the fully open position illustrated in FIG. 6A and the fully closed position illustrated in FIG. 6B. As best shown in FIGS. 6A and 6B, first trigger 150A has a first upper arcuate slot 156A and an opposing first lower arcuate slot 158A, and second trigger 150B likewise has a second upper arcuate slot 156B and an opposing second lower arcuate slot 158B. The terms "upper" and "lower" are intended only to distinguish one slot from another slot as such features appear in the drawings, and not as a limitation on the orientation of clip applier 100. The function of arcuate slots 156A, 156B, 158A, and 158B is described below.

As indicated by broken lines in FIG. 3, first and second shrouds 115A and 115B are assembled together, at least in part, by mating their respective posts 124A, 124B, 126, 126B, 130 and 136 with corresponding blind bores 141, 143, 145A, 145B, and 147. For example, post 124A of first shroud 115A is fitted into blind bore 141 of second shroud 115B, post 126A of first shroud 115A is fitted into blind bore 143 of second shroud 115B, and posts 128, 132, and 136 of second shroud 115B are fitted into corresponding blind bores (not shown) of first shroud 115A. In addition, at the proximal end of actuator assembly 110, a dowel 159 is press-fitted into engagement with blind bore 145 of second shroud 115B and opposing blind bore 148 (see FIGS. 6A and 6B) of first shroud 115A. In the conventional manner, one or more complementary outer ribs or walls 161A and 161B formed on first and second shrouds 115A and 115B can also be used to properly align and fit first and second shrouds 115A and 115B together. As further shown in FIG. 5, dowel 159 also serves as a proximal anchor for a coupling return spring 164, the function of which will be described below. In the assembly of clip applier 100, first and second triggers 150A and 150B are disposed side-by-side between first and second shrouds 115A and 115B, and extend transversely outwardly from lateral openings created by the mating of first and second shrouds 115A and 115B. Distally located posts 124A and 124B of first and second shrouds 115A and 115B extend through respective apertures 167A and 167B of first and second triggers 150A and 150B. By this configuration, first and second triggers 150A and 150B oppose each other and can be pivoted toward and away from each other in a scissors-like fashion about distally located posts 124A and 124B, respectively.

Referring to FIGS. 3, 5, 6A and 6B, actuator assembly 110 includes a carriage member or coupling, generally designated 170, that serves as a primary mechanical interface between actuator assembly 110 and channel assembly 250. In general terms, coupling 170 has a coupling base 172 from which two coupling posts 174A and 174B extend, a box section 176 with a pair of lateral slots 178A and 178B, a U-shaped proximal yoke 180, and a pair of opposing upper and lower U-shaped distal yokes 182 and 184. Coupling 170 has structural features (not specifically shown) that interact with certain ribs of first and second shrouds 115A and 115B to allow coupling 170 to be retained in proper alignment within the housing created by first and second shrouds 115A and 115B. At the same time, however, coupling 170 is permitted to axially slide within the housing during the forward and return strokes of actuator assembly 110, i.e., between the open position shown in FIG. 6A and the closed position shown in FIG. 6B. Coupling 170 is actuated along the axial direction by means of the pivoting of first and second triggers 150A and 150B, i.e., by the squeezing of actuator assembly 110 by the user, and the responsive action of four-bar linkage assembly 205 described below.

As further shown in FIG. 3, actuator assembly 110 also includes an anti-backup spring element, generally designated 190, secured in another slot (described below) of coupling 170 that is located on the side of box section 176 opposite to that containing lateral slots 178A and 178B. The details and function of anti-backup spring element 190 are described below.

Referring to FIGS. 3, 5, 6A and 6B, a four-bar linkage assembly, generally designated 205 in FIG. 5, serves as the preferred mechanical interface between first and second triggers 150A and 150B and coupling 170 for translating the pivoting motion of first and second triggers 150A and 150B into the responsive axial motion of coupling 170. The separate components of four-bar linkage assembly 205 are shown in exploded view in FIG. 3. Four-bar linkage assembly 205 is housed within actuator assembly 110, and comprises first and second front link bars 209A and 209B, first and second rear link bars 211A and 211B, and first and second trigger pins 213A and 213B. An aperture is formed at each end of each link bar 209A, 209B, 211A and 211B. The particular configuration of four-bar linkage assembly 205 enhances the mechanical advantage provided for actuating coupling 170 through the use of first and second triggers 150A and 150B.

Linkage assembly 205 is assembled as shown in FIG. 5. Specifically, one aperture of first front link bar 209A is pivotably mounted around one post 174A of coupling 170, and its other aperture is pivotably mounted around first trigger pin 213A. Similarly, one aperture of second front link bar 209B is pivotably mounted around the other post 174B of coupling 170, and its other aperture is pivotably mounted around second trigger pin 213B. One aperture of first rear link bar 211A is pivotably mounted around first trigger pin 213A, and its other aperture is pivotably mounted around post 126B of second shroud 115B. One aperture of second rear link bar 211B is pivotably mounted around second trigger pin 213B, and its other aperture is pivotably mounted around post 126A of first shroud 115A. First and second trigger pins 213A and 213B are movably supported in arcuate slots 156A, 156B, 158A and 158B of first and second triggers 150A and 150B, as shown in FIGS. 6A and 6B. Arcuate slots 156A, 156B, 158A, and 158B serve as cams to guide and coordinate the pivotal actuation of link bars 209A, 209B, 211A and 211B, and thus the axial actuation of coupling 170, between the fully open position shown in FIG. 6A and the fully closed position shown in FIG. 6B, all of which occurs in response to squeezing first and second triggers 150A and 150B toward each other. It will be noted that first and second triggers 150A and 150B have been rendered transparent in FIGS. 6A and 6B to illustrate the interaction between first and second trigger pins 213A and 213B and arcuate slots 156A, 156B, 158A and 158B. As also shown in FIGS. 6A and 6B, coupling return spring 164 is connected between dowel 159 of the housing and proximal yoke 180 of coupling 170 to bias actuator assembly 110 toward the open position. Preferably, at the fully open position, a portion of coupling 170 abuts post 130 (see FIG. 5) to prevent further rearward translation of coupling 170.

Referring now to FIGS. 3 and 4, channel assembly 250 comprises a hollow tube 260; a clip channel member, generally designated 280; and a walking beam or clip feed bar, generally designated 330, all of which preferably are formed and/or stamped from a suitable metal material. In assembling channel assembly 250, a number of clips CL (e.g., sixteen or seventeen) are loaded in series into channel member 280. Once clips CL have been loaded into channel member 280, feed bar 330 is fitted to channel member 280 so that clips CL are interposed between feeder bar 330 and channel member 280. Channel member 280 and feed bar 330 are then inserted into tube 260 with clips CL retained therein. As will become evident from the description hereinbelow, feed bar 330 is axially movable with respect to tube 260, and both feed bar 330 and tube 260 are axially movable with respect to channel member 280. Moreover, channel member 280 does not move in relation to either tube 260 or feed bar 330.

Referring particularly to FIG. 4, tube 260 includes first and second conformal wall sections 262 and 264 (see FIGS. 8A and 8B) to accommodate the profile of jaw assembly 375. As indicated by broken lines in FIG. 3 and also in FIG. 5, in assembling clip applier 100, tube 260 is inserted between first and second shrouds 115A and 115B and between upper and lower distal yokes 182 and 184 of coupling 170. An upper tube tab 266 (FIGS. 3 and 4) and a lower tube tab 268 (FIGS. 6A and 6B) are formed at the proximal end of tube 260. As evident from FIGS. 6A and 6B, during a given stroke of actuator assembly 110, each tube tab 266 and 268 is axially movable along the length of the central, elongate opening defined by one of distal yokes 182 or 184 of coupling 170. During the return stroke, one of distal yokes 182 or 184 engages the corresponding tube tab 266 or 268 to pull tube 260 back in the proximal direction. In addition, a tube return spring 271 is connected between post 136 of second shroud 115B (see FIG. 5) and an aperture 137 of tube 260 (see FIGS. 6A and 6B) to assist in pulling tube 260 back in the proximal direction during the return stroke. As described below, the distal actuation of tube 260 actuates jaw assembly 375 into its fully closed position for compressing a clip CL loaded therein, and the proximal retraction of tube 260 allows jaw assembly 375 to return to its fully open position.

Referring back to FIG. 4, channel member 280 comprises a base wall 282 and opposing first and second side walls 284 and 286 to form a generally C-shaped structure. A number of lateral channel tabs 288 (e.g., sixteen) are formed in base wall 282 along its length are angled toward feed bar 330, and are axially spaced at equal intervals from each other. Lateral channel tabs 288 assist in retaining clips CL at the index positions cooperatively defined by the various components of channel assembly 250. As clips CL are advanced by feed bar 330 along the length of channel member 280, clips CL come into sliding contact with corresponding lateral channel tabs 288 and flex in response to this contact. Once a clip CL has passed a lateral channel tab 288, lateral channel tab 288 snaps behind clip CL to prevent clip CL from moving backward to a preceding index position. At its proximal end, channel member 280 includes an extended portion of base wall 282 comprising a ratchet section 291 and a proximal aperture 295. Ratchet section 291 comprises a linear series of teeth 293 incrementally separated by open spaces. Ratchet section 291 advantageously interacts with anti-backup spring element 190 (see FIGS. 3, 6A and 6B) in a manner described below. As shown in FIGS. 3 and 5, proximal aperture 295 of channel member 280 is used to anchor channel member 280 to post 130 of second shroud 115B, thereby affixing the position of channel member 280 with respect to actuator assembly 110.

Referring back to FIG. 4, the distal end of channel member 280 is enclosed by mating a C-shaped channel piece 297 to first and second side walls 284 and 286. Channel piece 297 includes two opposing pairs of distal end tabs 301A and 301B and 303A and 303B that assist in guiding each clip CL through the transition from channel member 280 to jaw assembly 375 (see FIG. 3). Channel member 280 also includes a feed bar stop element 305 formed on second side wall 286 near its distal end. The function of feed bar stop element 305 is described below with reference to FIGS. 11A–11E. Channel member 280 further includes mounting features 307 and 309 for securing jaw assembly 375 to channel member 280. At a location near the distal end of channel member 280, first side wall 284 of channel member 280 defines a chicane 315 that protrudes radially outwardly in relation to the longitudinal axis of channel member 280. As described in more detail below, chicane 315 provides clearance for rotating or pivoting clips CL at the distal end of channel assembly 250 during the forward stroke of clip applier 100. As also described in more detail below, channel assembly 250 includes a clip retainer spring element, generally designated 320, that is secured to base wall 282 of channel member 280.

With continuing reference to FIG. 4, a number of lateral feed bar tabs 333 (e.g., sixteen) are formed in feed bar 330 along its length are angled toward channel member 280, and are axially spaced at equal intervals from each other. As best shown in the sequential, cross-sectional views of FIGS. 16A–16E, lateral feed bar tabs 333 cooperate with lateral channel tabs 288 to assist in retaining clips CL at the index positions of channel assembly 250. In addition, during forward axial movement of feed bar 330, lateral feed bar tabs 333 engage each clip CL stored in channel assembly 250 to move clip CL from a given index position to a succeeding index position. The axial forward movement of lateral feed bar tabs 333 in relation to lateral channel tabs 288 is shown in FIGS. 16A–16E. Referring back to FIG. 4, feed bar 330 includes an axial extension 335 and a wide wall section 337 at its proximal end. A pair of proximal feed bar tabs 339A and 339B are formed in wide wall section 337 on each side of axial extension 335. As evident in FIG. 3, in assembling clip applier 100, feed bar 330 is inserted between upper and lower distal yokes 182 and 184 of coupling 170 and into its box section 176. When so inserted, each proximal feed bar tab 339A and 339B is deflected into a corresponding lateral slot 178A and 178B of coupling 170. During the return stroke of actuator assembly 110, the distal ends of lateral slots 178A and 178B engage corresponding proximal feed bar tabs 339A and 339B to pull feed bar 330 back in the proximal direction. In addition, a feed bar spring 342 is mounted around axial extension 335 of feed bar 330. The proximal end of feed bar spring 342 contacts a conical internal surface of coupling 170 (described below with reference to FIGS. 16A–16E), and the distal end contacts edges 338A and 338B of wide wall section 337 of feed bar 330. Feed bar spring 342 maintains a biasing force on feed bar 330 in the forward axial direction.

At its distal end, feed bar 330 terminates at a clip driving tab 345 substantially disposed along the central longitudinal axis of feed bar 330, a clip rotating tab 347 disposed in off-axis parallel relation to clip driving tab 345, and a clip hold-down tab 349 disposed in off-axis parallel relation to clip driving tab 345 opposite to clip rotating tab 347. The respective functions and details of clip driving tab 345, clip rotating tab 347, and clip hold-down tab 349 are described below. A number of first outer wall sections 344A–C and second outer wall sections 346A–C are formed along the length of feed bar 330. First outer wall sections 344A–C ride along the outside of first side wall 284 of channel member 280, and second outer wall sections 346A–C ride along the outside of second side wall 286 (see, e.g., FIGS. 11A–11E).

During any given cycle of operation of clip applier 100, there is a forward stroke followed by a return stroke, as described in more detail below with reference to FIGS. 11A–11E and 16A–16E. It can be seen from FIGS. 6A and 6B that four-bar linkage 205 directly interconnects first and second triggers 150A and 150B with coupling 170. Thus, any pivotal movement of triggers 150A and 150B, whether by squeezing (i.e., forward stroke) or releasing (i.e., return stroke) first and second triggers 150A and 150B, will result in axial movement of coupling 170 in either the forward direction (from squeezing triggers) or rearward direction (from releasing triggers). Accordingly, there is in effect a one-to-one correspondence between the stroke of actuator assembly 110 and the responsive axial translation of coupling 170. This is not true, however, for feed bar 330 and tube 260. Because feed bar 330 and tube 260 are connected differently to coupling 170, they are pushed forwardly (i.e., extended from actuator assembly 110) and pulled rearwardly (i.e., retracted into actuator assembly 110) at different times and over different time intervals, both relative to each other and relative to the coupling.

As regards the forward stroke of actuator assembly 110, there are two stages during any given cycle of operation of clip applier 100. The first stage loads the most distal clip stored in channel assembly 250 into jaw assembly 375, performs operations on the next two clips to prepare them for loading into jaw assembly during the next two cycles, and advances all other clips stored in channel assembly 250 by one incremental step. It will be noted that in the open position shown in FIG. 6A, box section 176 of coupling 170 is separated by a distance from the proximal end of tube 260. This separation distance roughly corresponds to the distance over which coupling 170 travels during the first stage of the forward stroke. Thus, during the first stage of the forward stroke in which first and second triggers 150A and 150B begin to pivot towards each other, coupling 170 moves forwardly toward tube 260 but does not contact tube 260 (or at least not enough to be able to push tube 260). Accordingly, tube 260 is not actuated during this first stage of the forward stroke. Also during the first stage of the forward stroke, however, an internal surface of coupling 170 in combination with the forward bias of feed bar spring 342 does begin to advance feed bar 330 in the forward direction. In this manner, the user can squeeze triggers 150A and 150B to advance a clip CL into jaw assembly 375 without actuating jaw assembly 375. Thus, while the first stage of the forward stroke entails feeding the most distal clip CL (or last clip lockout element 355, shown in FIGS. 3 and 4 and described below) into jaw assembly 375 and advancing the remaining clips CL of the stack by one increment along channel assembly 250, the first stage does not entail compressing and latching a clip CL onto tissue.

As shown in FIG. 6B, the second stage of the forward stroke is effected by further squeezing of triggers 150A and 150B, and thus further pivoting of triggers 150A and 150B toward each other and further axial movement of coupling 170. Box section 176 of coupling 170 contacts tube 260 during the second stage, thereby causing tube 260 to move forwardly. As described in more detail below with reference to FIGS. 8A and 8B, the forward movement of tube 260 in relation to jaw assembly 375 in turn causes jaw assembly 375 to compress a clip CL (which has been previously loaded therein by the forward movement of feed bar 330 during the first stage). During the second stage, the forward motion of feed bar 330 is stopped through mechanisms described below in connection with FIGS. 11A–11E.

As regards the return stroke of actuator assembly 110, it is evident from FIGS. 6A and 6B that the release of the user's hand pressure on actuator assembly 110 allows coupling return spring 164—by its connection with proximal yoke 180 of coupling 170—to pull coupling 170 back in the proximal direction. Due to the interconnection provided by four-bar linkage 205, this in turn causes first and second triggers 150A and 150B to pivot away from each other. Tube 260 also begins to be pulled back with coupling 170, due to the use of tube return spring 271 and because the U-shaped distal ends of distal yokes 182 and 184 of coupling 170 eventually engage tube tabs 266 and 268, respectively. In an analogous manner, feed bar 330 is eventually pulled back with coupling 170 due to the interaction between proximal feed bar tabs 339A and 339B and lateral slots 178A and 178B of coupling 170, respectively.

As further illustrated in FIGS. 3 and 4, clip applier 100 includes a locking feature in the form of a last-clip lockout element 355, which preferably is constructed from a suitable polymeric material. Last-clip lockout element 355 is loaded into channel member 280 after the last (i.e., most proximally located) clip CL. Last clip lockout element 355 is, in general, dimensionally similar to clips CL and includes boss sections 357 and 359 similar to bosses 62/64 and 56/58 of clips CL illustrated in FIGS. 1A and 1B. Hence, last clip lockout element 355 is conveyed along channel assembly 250 from one index to position to another in the same manner as clips CL. In the use of clip applier 100, after the last clip has been loaded into jaw assembly 375 and applied at a surgical site, further attempted use of clip applier 100 will result in last clip lockout element 355 being loaded into jaw assembly 375. Unlike clips CL, however, last clip lockout element 355 has a rigid, solid form and thus cannot be compressed by jaw assembly 375. Thus, the loading of last clip lockout element 355 into jaw assembly 375 prevents further actuation of first and second triggers 150A and 150B, thereby effectively locking clip applier 100 and indicating to the user that all clips CL initially provided with clip applier 100 have been used. For this purpose, it is also preferable that last clip lockout element 355 be colored differently from clips CL and the various components of clip applier 100.

Figure 7:
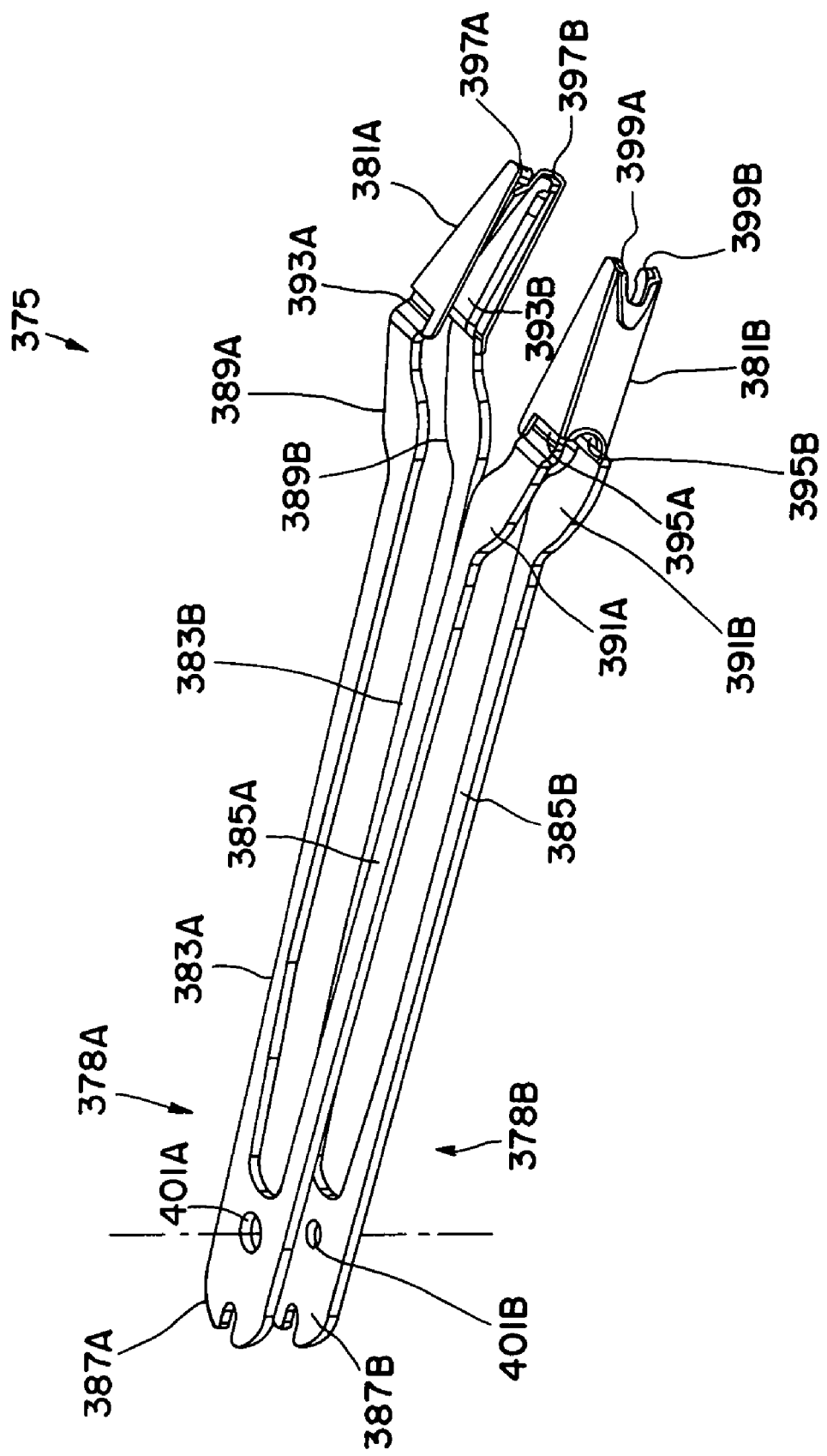
FIG. 7 is a perspective view of the jaw assembly provided with the clip applier.

Referring now to FIG. 7, jaw assembly 375 comprises first and second resilient jaw structural halves, generally designated 378A and 378B, connected together at their distal ends by first and second jaw channels 381A and 381B. The distal features of jaw assembly 375 are designed to advantageously engage bosses 56, 58, 62 and 64 of clip CL and to and retain first and second legs 22 and 24 of clip CL (see FIGS. 1A and 1B), such that the alignment of clip CL with respect to jaw channels 381A and 381B is maintained. First resilient jaw half 378A includes a pair of opposing first jaw arms 383A and 385A joined at a first base region 387A. First jaw arms 383A and 385A respectively transition to a pair of opposing first cam sections 389A and 391A, which in turn respectively transition to a pair of opposing first jaw members 393A and 395A. First jaw members 393A and 395A terminate in first jaw hooks 397A and 399A at their distal ends. Second resilient jaw member 378B is similar or identical to first resilient jaw member 378A, and thus includes a pair of opposing second jaw arms 383B and 385B joined at a second base region 387B. Second jaw arms 383B and 385B also respectively transition to a pair of opposing second cam sections 389B and 391B, which in turn respectively transition to a pair of opposing second jaw members 393B and 395B. Second jaw members 393B and 395B terminate, in second jaw hooks 397B and 399B at their distal ends.

With continuing reference to FIG. 7, first and second jaw hooks 397A/399A and 397B/399B assist in engaging and retaining bosses 56, 58, 62 and 64 of a clip CL (see FIGS. 1A and 1B) in a controlled manner. First and second jaw channels 381A and 381B assist in engaging and maintaining the proper alignment of legs 22 and 24 of clip CL. Each resilient jaw half 378A or 378B is dimensioned to enable its respective jaw arms 383A/385A and 383B/385B to be deflected toward and away from each other with respect to its respective base region 387A and 387B, with each pair of jaw arms 383A/385A and 383B/385B being spring-biased away from each other. As a result, the jaws formed by the distal features of jaw assembly 375 are movable between open and closed positions, and are spring-biased toward the open position. First and second base regions 387A and 387B have respective first and second apertures 401A and 401B, which may or may not be similarly sized. As indicated by broken lines in FIG. 3, first and second apertures 401A and 401B are respectively fitted around mounting features 307 and 309 of channel member 280 to anchor jaw assembly 375 to channel member 280. Accordingly, tube 260 and feed bar 330 move axially with respect to jaw assembly 375 as well as channel member 280.

Figure 8A:
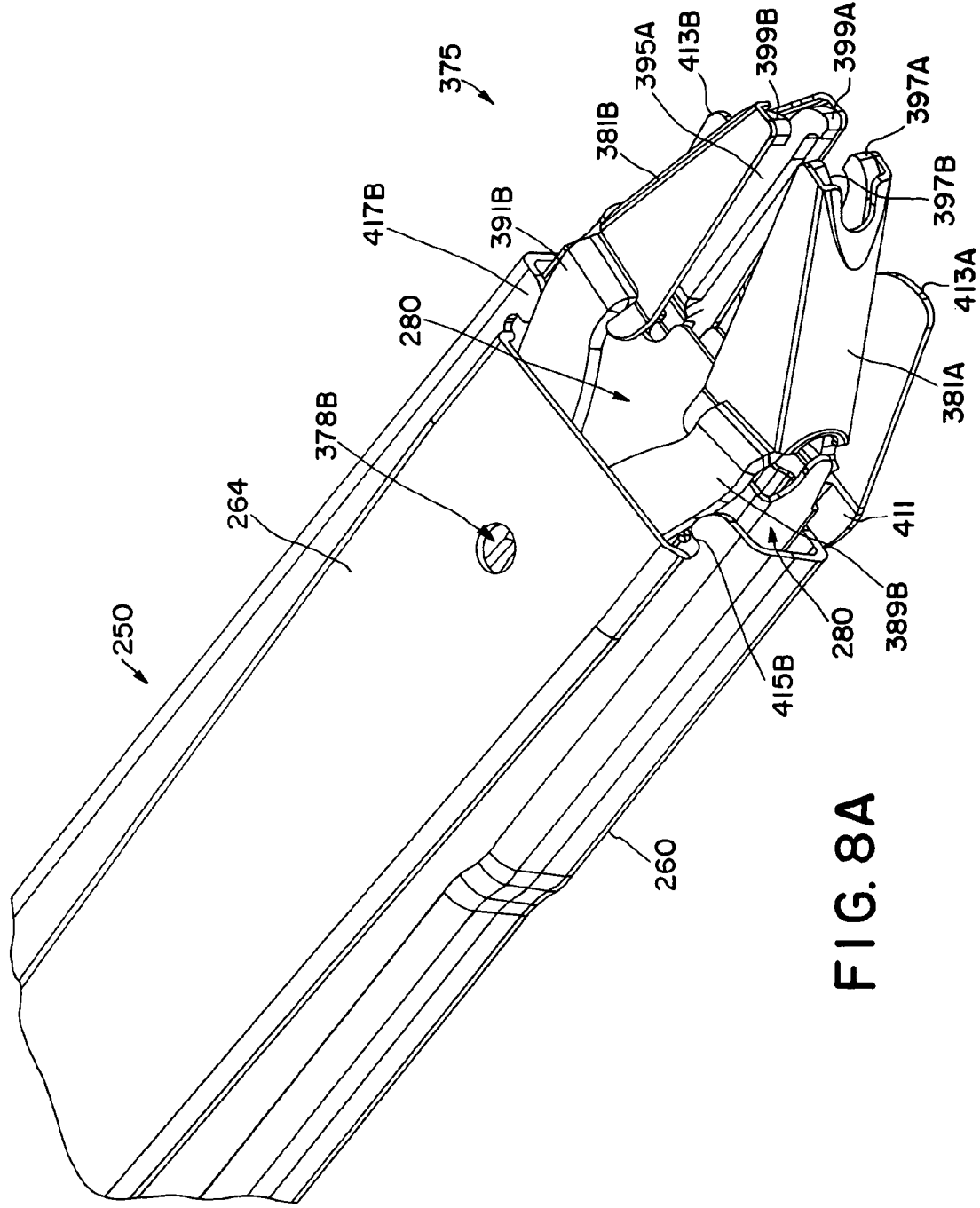
FIGS. 8A and 8B are perspective views of each side, respectively, of the distal end of the clip applier showing the jaw assembly in a closed position.
Figure 8B:
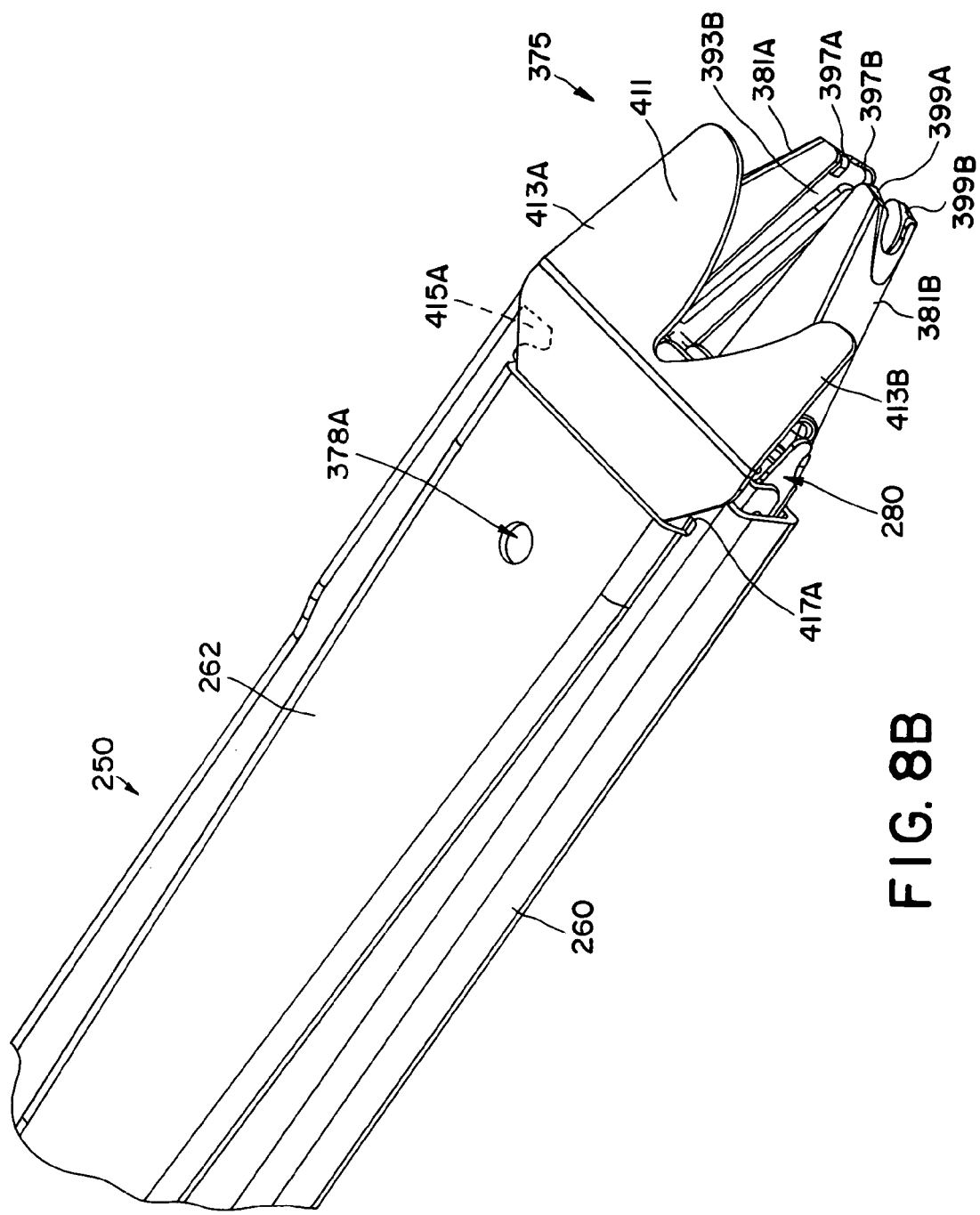

FIGS. 8A and 8B illustrate the distal end of channel assembly 250 and jaw assembly 375 while actuator assembly 110 is in the fully closed position (see, e.g., FIG. 6B), which also corresponds to the fully closed position of jaw assembly 375. As shown in FIGS. 8A and 8B, channel member 280 is interposed between first and second jaw halves 378A and 378B, and first and second jaw halves 378A and 378B are interposed between channel member 280 and tube 260. Conformal wall sections 262 and 264 of tube 260 provide clearance for first and second jaw halves 378A and 378B. As further shown in FIG. 8B, a tissue guide member 411 can be inserted between first conformal wall section 262 and second jaw half 378B. Tissue guide member 411 includes two rounded-edge fingers 413A and 413B that generally are disposed over a broader space than the distal end of jaw assembly 375. Tissue guide member 411 assists the user of clip applier 100 in manipulating jaw assembly 375 into a proper position around a target tissue to be ligated, such as by moving other adjoining or obstructing tissues out of the way of jaw assembly 375 or by separating such other tissues from the target tissue.

With continuing reference to FIGS. 7, 8A and 8B, clip applier 100 provides a four-point camming system for actuating jaw assembly 375 into the closed position. This system includes the pairs of first and second cam sections 389A/391A and 389B/391B of jaw assembly 375, and four inwardly facing tube tabs 415A, 415B, 417A and 417B formed at the distal end of tube 260. At any position of first and second triggers 150A and 150B of actuator assembly 110, each inwardly facing tube tab 415A, 415B, 417A and 417B contacts a corresponding one of cam sections 389A, 389B, 391A and 391B. As described previously, the forward stroke of actuator assembly 110 causes axial translation of tube 260 in the forward direction. At the same time, however, the axial position of jaw assembly 375 relative to tube 260 is fixed, because jaw assembly 375 is affixed to channel member 280 and channel member 280 is in turn affixed to a non-movable portion of actuator assembly 110. By comparing the closed position of jaw assembly 375 shown in FIGS. 8A and 8B with the open position of jaw assembly 375 shown in FIG. 2, it can be seen that the axial movement of tube 260 with respect to jaw assembly 375 causes inwardly facing tube tabs 415A, 415B, 417A and 417B to slide along cam sections 389A, 389B, 391A and 391B of jaw assembly 375, respectively. Since cam sections 389A, 389B, 391A and 391B are obliquely oriented in relation to the longitudinal axis of tube 260, inwardly facing tube tabs 415A, 415B, 417A and 417B bear against cam sections 389A, 389B, 391A and 391B to cause corresponding first and second jaw arms 383A and 385A and 383B and 385B and first and second jaw channels 381A and 381B to pivot toward each other, thereby enabling a clip CL residing in jaw assembly 375 to be compressed.

FIGS. 8A and 8B illustrate two additional advantageous features of jaw assembly 375. In the fully closed state of jaw assembly 375, the jaws (i.e., first and second jaw members 393A/395A and 393B/395B and first and second jaw channels 381A and 381B) do not contact each other at any location thereof. Instead, a gap is maintained between the jaws even at the fully closed state of jaw assembly 375. This feature renders jaw assembly 375 atraumatic in that the components of jaw assembly 375 are preventing from damaging tissue. Moreover, it will be noted that the jaws are angled with respect to channel assembly 250, for example at about fifteen degrees from the central axis of channel assembly 250. The angled orientation of the jaws improves visibility of the target tissue during clip placement.

Referring now to FIGS. 9–11E, the invention provides a clip control system at the distal end of clip applier 100 for advantageously controlling the serial transition and loading of clips CL from channel assembly 250 to jaw assembly 375. The clip control system is realized primarily from the respective designs of afore-mentioned clip retainer spring element 320 and chicane 315 located at the distal region of channel member 280, and the interaction of these two components with feed bar 330 and clips CL. One advantageous feature of the clip control system is the use of four clip contact points or areas, represented by clip contact surfaces A, B, C and D in FIGS. 9 and 10.

Figure 9:
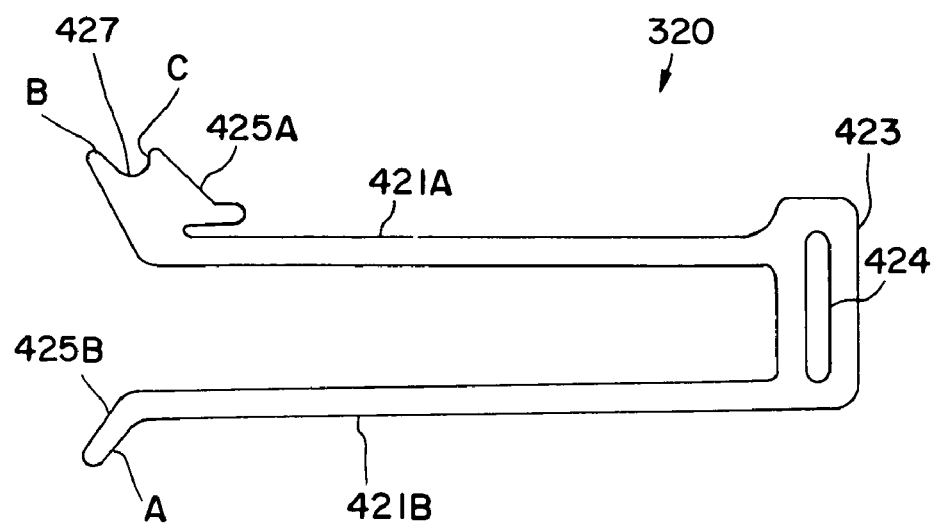
FIG. 9 is a side elevation view of a clip retainer spring element provided with the clip applier in accordance with the present invention.
Figure 10:
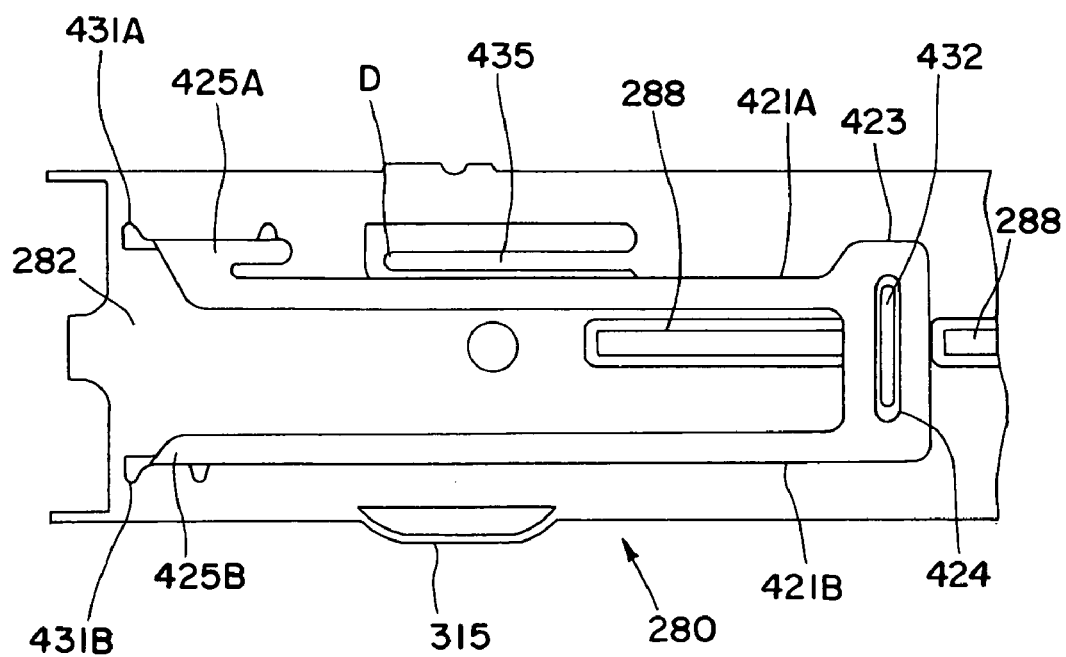
FIG. 10 is a side elevation view of the clip retainer spring element illustrated in FIG. 9, wherein the spring element has been attached to a channel member provided with the channel assembly of the clip applier.
Figure 11A:
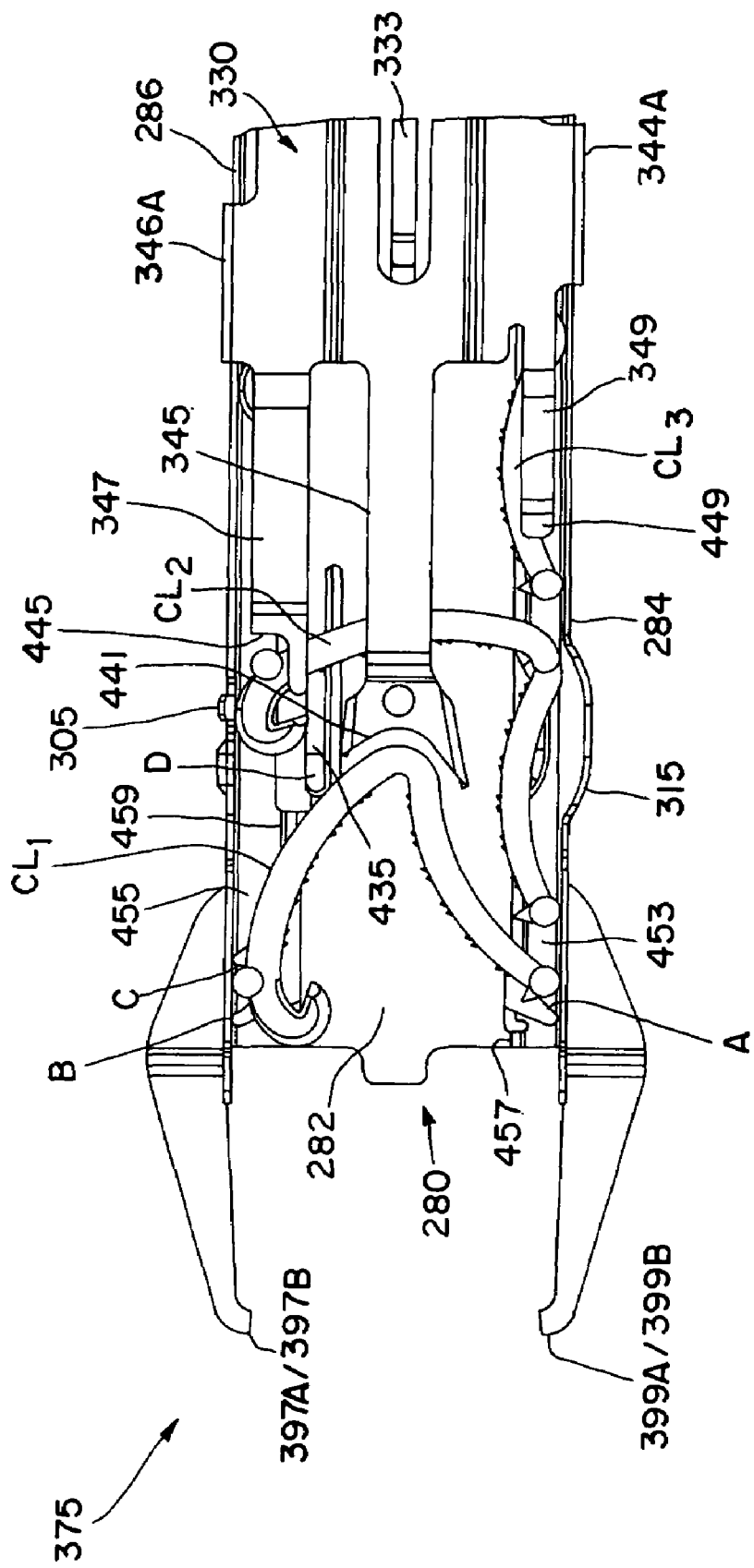

As shown in FIG. 9, the structure of clip retainer spring element 320 comprises a first spring arm 421A and a parallel second spring arm 421B joined at a bridge section 423. A slot 424 is formed in bridge section 423. First spring arm 421A terminates at a first distal end 425A that turns radially outwardly. First distal end 425A includes a recess or saddle 427, the sides of which constitute clip contact surfaces B and C. Second spring arm 421B terminates at a second distal end 425B that turns radially outwardly in an orientation opposite to that of first distal end 425A. One of the edges of second distal end 425B constitutes clip contact surface A. As shown in FIG. 10, first and second distal openings 431A and 431B and a protrusion or tab 432 are formed in base wall 282 of channel member 280. Clip retainer spring element 320 is secured against an outer surface of base wall 282 by inserting first and second distal ends 425A and 425B through first and second distal openings 431A and 431B of channel member 280, respectively, with protrusion or tab 432 extending through slot 424. Accordingly, first and second distal ends 425A and 425B extend into the interior of channel member 280 where clips CL are located, as shown for example in FIG. 11A. As also shown in FIGS. 10 and 11A, channel member 280 includes a clip control tab 435 that is offset from lateral channel tabs 288. Clip control tab 435 has a tip bent inwardly toward the channel interior. The tip of clip control tab 435 constitutes clip control surface D.

Figure 11B:
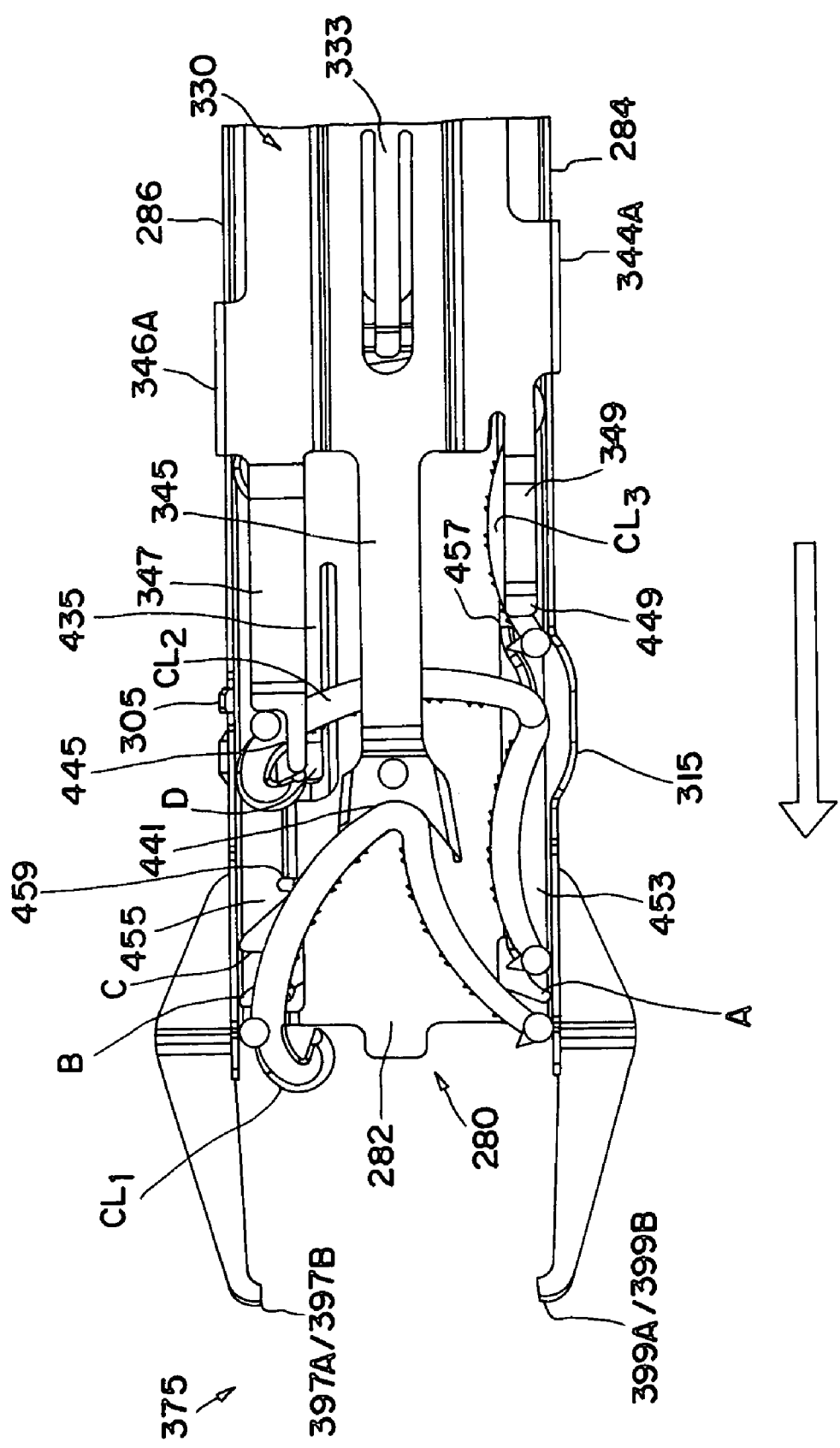

The operation of the clip control system will now be described with reference primarily being made to the sequential views of FIGS. 11A–11E. For the purpose of the present description, the first three clips in the series of clips CL loaded within channel assembly 250 are designated as first clip $CL_1$, second clip $CL_2$, and third clip $CL_3$ in FIGS. 11A–11E. The structural details of these clips $CL_1$, $CL_2$ and $CL_3$ can be similar to those of clip CL described above by way of example in connection with FIGS. 1A and 1B. FIG. 11A highlights the structural details of clip driving tab 345, clip rotating tab 347, and clip hold-down tab 349 of feed bar 330. The tip of clip driving tab 345 forms a saddle-shaped recess 441 that substantially conforms to the hinge section of each clip $CL_1$, $CL_2$ and $CL_3$. By providing one or more bends in clip driving tab 345, the portion of clip driving tab 345 containing saddle-shaped recess 441 is closer to base wall 282 of channel member 280 than the remaining elongate portion of clip driving tab 345. This configuration enables clip driving tab 345 to engage hinge section of first clip CL, without being impeded by the presence of second and third clips $CL_2$ and $CL_3$. The tip of clip rotating tab 347 forms an L-shaped recess 445 adapted for engaging one of the bosses on the hook end of each clip CL when in the position of second clip $CL_2$ as shown in FIG. 11B, i.e., the second position in the stack of clips CL. The tip of clip rotating tab 347 is also angled inwardly to assist in retaining clips $CL_1$, $CL_2$ and $CL_3$ against the inside surface of base wall 282 of channel member 280. Clip hold-down tab 349 terminates at a bent tip 449 that is angled inwardly toward the channel interior for engaging one of the lateral sides of clip $CL_1$, $CL_2$ or $CL_3$.

As also shown in FIG. 11A, first and second tracks 453 and 455 are formed along the length of the inside surface of base wall 282 of channel member 280, near first and second side walls 284 and 286, respectively. One of the bosses of the double-tooth side of each clip CL is guided along first track 453, and one of the bosses of the hook side of each clip CL is guided along second track 455. First and second tracks 453 and 455 are respectively defined by forming first and second axial ribs 457 and 459 on base wall 282 parallel to first and second walls 284 and 286. The portion of first axial rib 457 adjacent to chicane 315 of first side wall 284 deviates transversely outwardly with chicane 315 in relation to the longitudinal axis of channel member 280. Thus, a chicane section of first track 453 is defined to provide a deviating path for the double-tooth side of clips $CL_1$, $CL_2$ and $CL_3$, for a purpose described below.

In FIG. 11A, third clip $CL_3$ is illustrated in the normal position taken by the stacked clips CL at their respective index positions along the length of channel member 280, with its hook section in sliding contact with second side wall 286 of channel member 280 and its double-tooth and hinge sections in sliding contact with first side wall 284. However, third clip $CL_3$ has been advanced to a position at which clip hold-down tab 349 of feed bar 330 engages one of the lateral sides of third clip $CL_3$. Further movement of feed bar 330 will cause the most distal lateral feed bar tab 333 to drive third clip $CL_3$ forwardly. Second clip $CL_2$ is illustrated in a position just prior to being rotated. At this position, the hinge section of second clip $CL_2$ is about to enter the area of chicane 315, and one of the bosses on the hook side of second clip $CL_2$ is about to be engaged by clip rotating tab 347 of feed bar 330. First clip $CL_1$ is illustrated in a rotated position that enables it to be advanced into jaw assembly 375 by clip driving tab 345 of feed bar 330, and that enables jaw hooks 397A/399A and 397B/399B to properly engage the bosses of first clip $CL_1$ (see FIG. 11E). One of the bosses on the hook side of first clip $CL_1$ is retained between clip control surfaces B and C of first distal end of clip retainer spring element 320, and one of the bosses on the double-tooth side of first clip $CL_1$ is retained by clip control surface A of clip retainer spring element 320. Clip control surface D, having sprung further into the interior of channel member 280 after advancement of first clip $CL_1$, engages the back side of first clip $CL_1$. In this manner, first clip $CL_1$ is fully stabilized in preparation for being driven into jaw assembly 375.

Referring to FIG. 11B, feed bar 330 has been actuated forwardly in response to the forward stroke of actuator assembly 110. A number of events occur simultaneously in response to the movement of feed bar 330 in the distal direction. Clip driving tab 345 contacts hinge section of first clip $CL_1$ and begins to drive first clip $CL_1$ distally into jaw assembly 375. First clip $CL_1$ will continue to be driven into jaw assembly 375 (see FIGS. 11C and 11D) until its bosses encounter jaw hooks 397A/399A and 397B/399B (see FIG. 11E). At the same time, clip rotating tab 347 contacts one of the hook-side bosses of second clip $CL_2$ and begins to drive second clip $CL_2$ distally. In the case of second clip $CL_2$, however, one of its double-tooth-side bosses eventually engages clip control surface A of clip retainer spring element 320, at which point the forward movement of second clip $CL_2$ is altered. A primary function of clip control surface A is to resist the load applied by double-tooth side of second clip $CL_2$ so that its movement ceases relative to the hook side. The retention of the double-tooth-side boss of second clip $CL_2$ by clip control surface A creates a pivot point at the double-tooth-side boss. As a result, the continued forward motion of feed bar 330 causes clip rotating tab 347 to drive the hook side of second clip $CL_2$ forward, thereby rotating second clip $CL_2$ in the counterclockwise direction about the pivot point of its double-tooth-side boss. At the completion of the rotation of second clip $CL_2$, second clip $CL_2$ will be staged between clip control surfaces B and C for firing into jaw assembly 375 during the next cycle. That is, as described further below, second clip $CL_2$ will eventually assume the position of first clip $CL_1$ shown in FIG. 11A. While these operations are occurring on first and second clips $CL_1$ and $CL_2$, the most distal lateral feed bar tab 333 contacts third clip $CL_3$ and drives it to the pre-rotation stage shown in FIG. 11B. In addition, clip hold-down tab 349 keeps third clip $CL_3$ properly seated within the channel interior. It will be understood that all other clips of the stack loaded in channel assembly 250 are incrementally driven in the distal direction by other corresponding lateral feed bar tabs 333.

Referring to FIG. 11C, clip driving tab 345 continues to drive first clip $CL_1$ further into jaw assembly 375. While this is occurring, clip rotating tab 347 continues to drive the hook side of second clip $CL_2$ forwardly, and second clip $CL_2$ begins to rotate about the pivot point created through the engagement of its double-tooth-side boss and clip control surface A. This causes the hinge region of second clip $CL_2$ to move toward the central region of channel member 280 between its first and second side walls 284 and 286. Clip rotating tab 347 also continues to bias second clip $CL_2$ against base wall 282 of channel member 280 to maintain proper seating. In addition, third clip $CL_3$ continues to be driven forward by the most distal lateral feed bar tab 333 and to be biased by clip hold-down tab 349. The double-tooth side of third clip $CL_3$ enters chicane 315 formed in second side wall 286 of channel member 280. It can thus be seen that chicane 315 provides the clearance necessary for the double-tooth side of third clip $CL_3$ to bypass hinge section of second clip $CL_2$ while second clip $CL_2$ is rotating. Moreover, the presence of chicane 315 allows the incremental distance between clips CL in the stack to be reduced, thereby allowing a shorter clip stack and thus a shorter channel assembly 250.

Figure 11D:
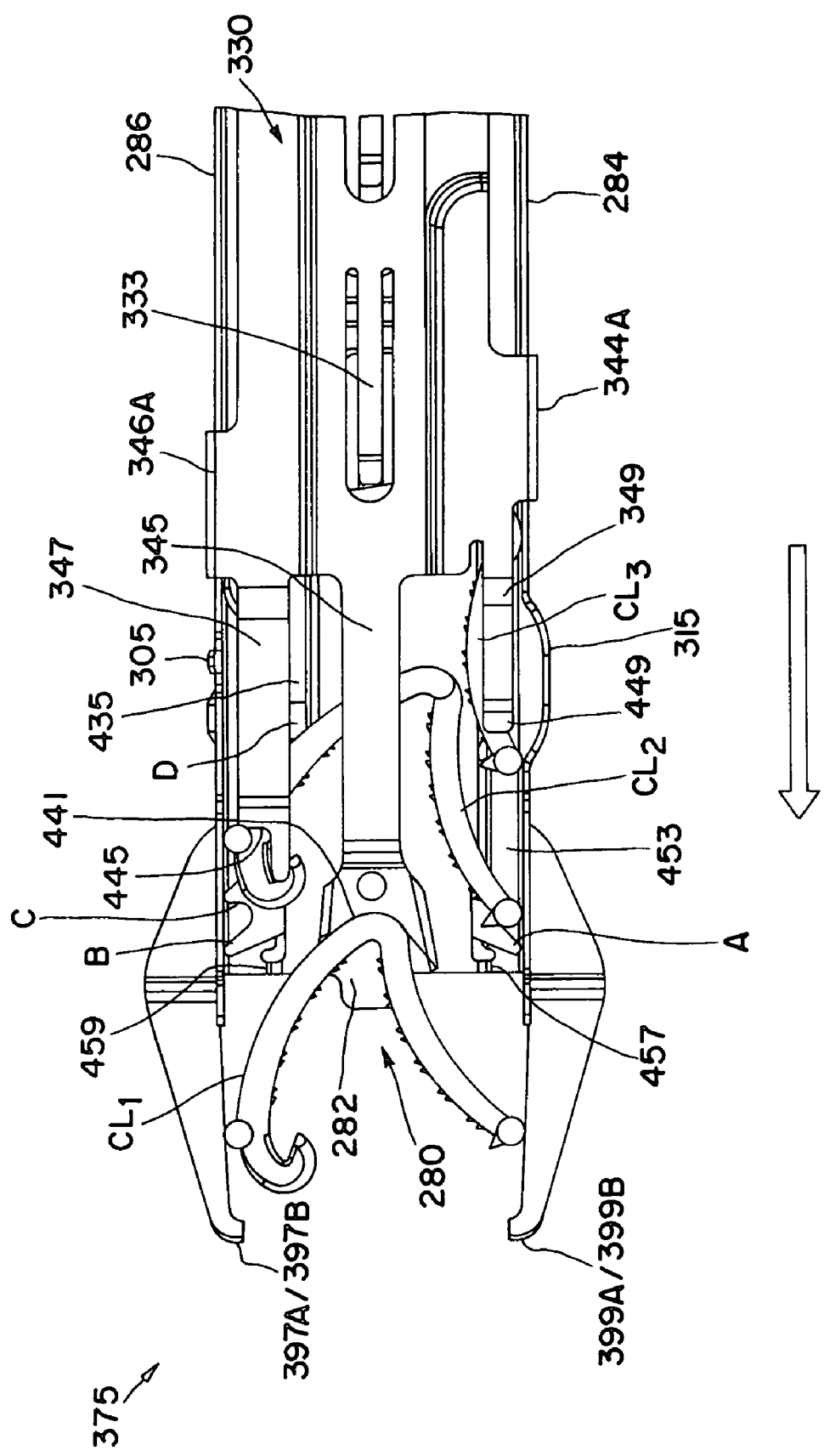

Referring to FIG. 11D, clip driving tab 345 continues to drive first clip $CL_1$ further into jaw assembly 375, and clip rotating tab 347 continues to rotate second clip $CL_2$ and bias second clip $CL_2$ against base wall 282 of channel member 280. Third clip continues to be driven forward by the most distal lateral feed bar tab 333 and to be biased by clip hold-down tab 349. The double-tooth side of third clip $CL_3$ has now completed its path through chicane 315. As a result, third clip $CL_3$ is positioned in close proximity to second clip $CL_2$, with hinge section of second clip $CL_2$ disposed well into the space between the legs of third clip $CL_3$.

Figure 11E:
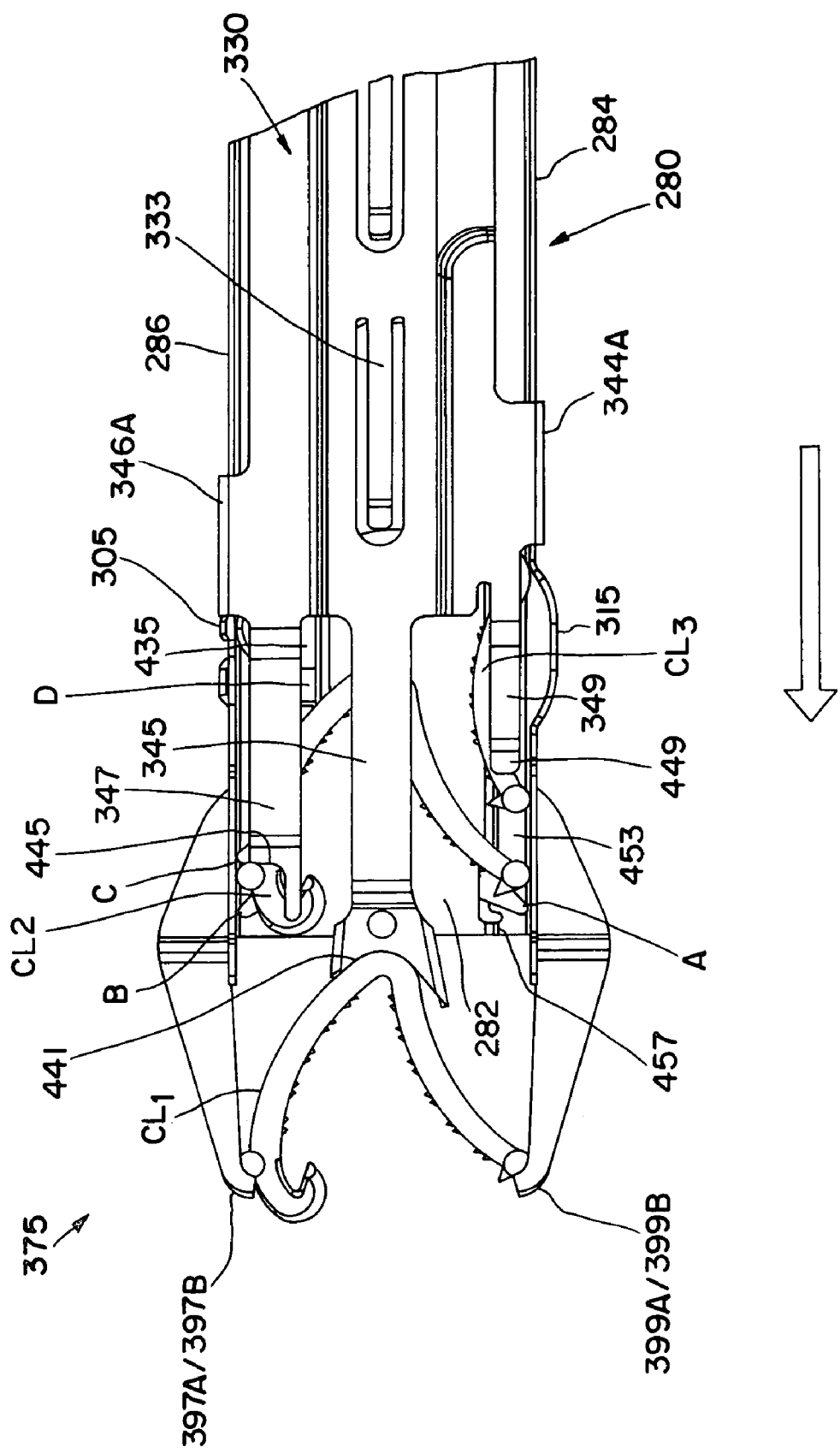

Referring to FIG. 11E, clip driving tab 345 has fully loaded first clip $CL_1$ into jaw assembly 375, such that its bosses engage and are held by jaw hooks 397A/399A and 397B/399B in a controlled manner. Clip rotating tab 347 has completed the rotation of second clip $CL_2$. At this position, the hook-side boss of second clip $CL_2$ facing base wall 282 of channel member 280 has been driven by clip rotating tab 347 into engagement between clip control surfaces B and C of clip retainer spring element 320. The inwardly angled tip of clip rotation tab 347 assists in retaining the hook-side boss of second clip $CL_2$ against base wall 282 while this boss is held in engagement between clip control surfaces B and C. Moreover, second clip $CL_2$ is prevented from rotating either clockwise or counterclockwise through its contact with clip control surface A of clip retainer spring element 320 and clip control surface D of clip control tab 435 of channel member

280. Second clip $CL_2$ is prevented from ever rotating when feed bar 330 abuts against feed bar stop element 305 of channel member 280, as described below.

It can be seen in FIG. 11E that second clip $CL_2$ is now staged in a proper position for being fired into jaw assembly 375 during the next cycle, and is in the same position as that previously attained by first clip $CL_1$ and shown in FIG. 11A. Second clip $CL_2$ is held in the pre-firing position illustrated in FIG. 11E until the occurrence of the next cycle. The next cycle will occur after actuator assembly 110 has been fully actuated by the user to compress first clip $CL_1$ into latching or locking engagement with a target vessel, and after the ensuing return stroke has been completed. Full actuation of actuator assembly 110 occurs when first and second triggers 150A and 150B have been squeezed to their fully closed position shown in FIG. 6B, which corresponds to the fully closed position of jaw assembly 375 shown in FIGS. 8A and 8B. During the return stroke of actuator assembly 110, feed bar 330 will be retracted in the proximal direction and its clip driving tab 345 will pass over or across the lateral side of second clip $CL_2$. Clip driving tab 345 may be deflected slightly in the direction away from base wall 282 of channel member 280 during the return stroke while it passes second clip $CL_2$ in this manner. During the forward stroke of the succeeding cycle, clip driving tab 345 will again be actuated forwardly, but will then engage second clip $CL_2$ in the same manner as illustrated for first clip $CL_1$ in FIG. 11B to drive second clip $CL_2$ into jaw assembly 375. It can be further observed in FIG. 11E that forward motion of third clip $CL_3$ continues to be controlled by the most distal lateral feed bar tab 333, and that third clip $CL_3$ continues to be biased by clip hold-down tab 349. As also shown in FIG. 11E, third clip $CL_3$ has now reached the prerotation zone previously occupied by second clip $CL_2$ in FIG. 11A.

It can also be seen in FIG. 11E that once first clip $CL_1$ has been driven into its fully loaded position in jaw assembly 375, the driving force imparted by clip driving tab 345 of feed bar 330 must cease. This is to prevent first clip $CL_1$ from being ejected from jaw assembly 375 and to permit first clip $CL_1$ to be freely manipulated prior to its application to a target vessel. However, further actuation by actuator assembly 110 is necessary to cause tube 260 to close jaw assembly 375 once the user of clip applier 100 is ready to latch first clip $CL_1$ to the target vessel. Thus, once first clip $CL_1$ has reached its fully loaded position, further forward motion of feed bar 330 must be prevented while further forward motion of tube 260 relative to feed bar 330 must be allowed. This requirement is met by the fact that proximal feed bar tabs 339A and 339B engage coupling 170 at lateral slots 178A and 178B (see, e.g., FIG. 14A), such that feed bar 330 is not directly affixed to coupling 170. In its fully loaded position shown in FIG. 11E, the bosses of first clip $CL_1$ engage jaw hooks 397A/399A and 397B/399B, which produces a reaction force opposing the driving force imparted by feed bar 330. This reaction force is able to defeat the forward driving force, and thus jaw hooks 397A/399A and 397B/399B are able to hold first clip $CL_1$ and stop feed bar 330, because proximal feed bar tabs 339A and 339B will slide along lateral slots 178A and 178B as coupling 170 continues to move forward to engage and drive tube 260.

At the completion of the forward stroke, however, first clip $CL_1$ is applied to the target vessel and hence no longer resides within jaw assembly 375 between jaw hooks 397A/399A and 397B/399B and clip driving tab 345. At this point, jaw hooks 397A/399A and 397B/399B can no longer function to prevent feed bar 330 from moving forwardly. As previously indicated, feed bar 330 is biased in the distal direction through the use of feed bar spring 342 (see FIG. 3). Accordingly, after first clip $CL_1$ has been applied, feed bar 330 again must be prevented from moving excessively forwardly, which might cause second clip $CL_2$ to become disengaged from clip control surfaces B and C and/or become overrotated. This requirement is met through the use of feed bar stop element 305. As shown in FIG. 11E, the most distal second outer wall section 346A of feed bar 330 comes into contact with feed bar stop element 305, thereby preventing further forward motion of feed bar 330 along the length of channel member 280.

The indexing of the stack of clips CL (see FIGS. 3 and 4) along the course of channel assembly 250, and the operation of the clip control system as described above with reference to FIGS. 11A–11E, occur for a number of cycles corresponding to the number of clips CL stored in clip channel assembly 250 prior to use of clip applier 100. As described above, once the last remaining clip CL has been loaded into jaw assembly 375 and latched to a target tissue, further stroking of actuator assembly 110 results in the firing of last-clip lockout element 355 (see FIGS. 3 and 4) into jaw assembly 375. Last-clip lockout element 355 effectively fills the space between first and second jaw members 393A/395A and 393B/395B, preventing further actuation of actuator assembly 110 and jaw assembly 375 and thus further use of clip applier 100. Clip applier 100 can be discarded at this time.

Referring now to FIGS. 12–16E, the invention provides a stroke control system that enables the user of clip applier 100 to repeatedly actuate actuator assembly 110 for any desired number to times prior to latching a clip CL (having previously been loaded into jaw assembly 375) around the target tissue. That is, the stroke control system enables the user to repeatedly perform partial forward strokes of actuator assembly 110 in order to manipulate, adjust, and/or compress clip CL as needed for optimizing the surgical procedure. The stroke control system also has anti-backup and ratcheting features that prevent the user from unintentionally or mistakenly resetting clip applier 100 during the first stage of the forward stroke and prior to completion of the second stage. The system is realized primarily from the unique design of the afore-mentioned anti-backup spring element 190, as well as its interaction with ratchet section of channel member 280 and certain features of second shroud 115B (as described below).

Figure 12:
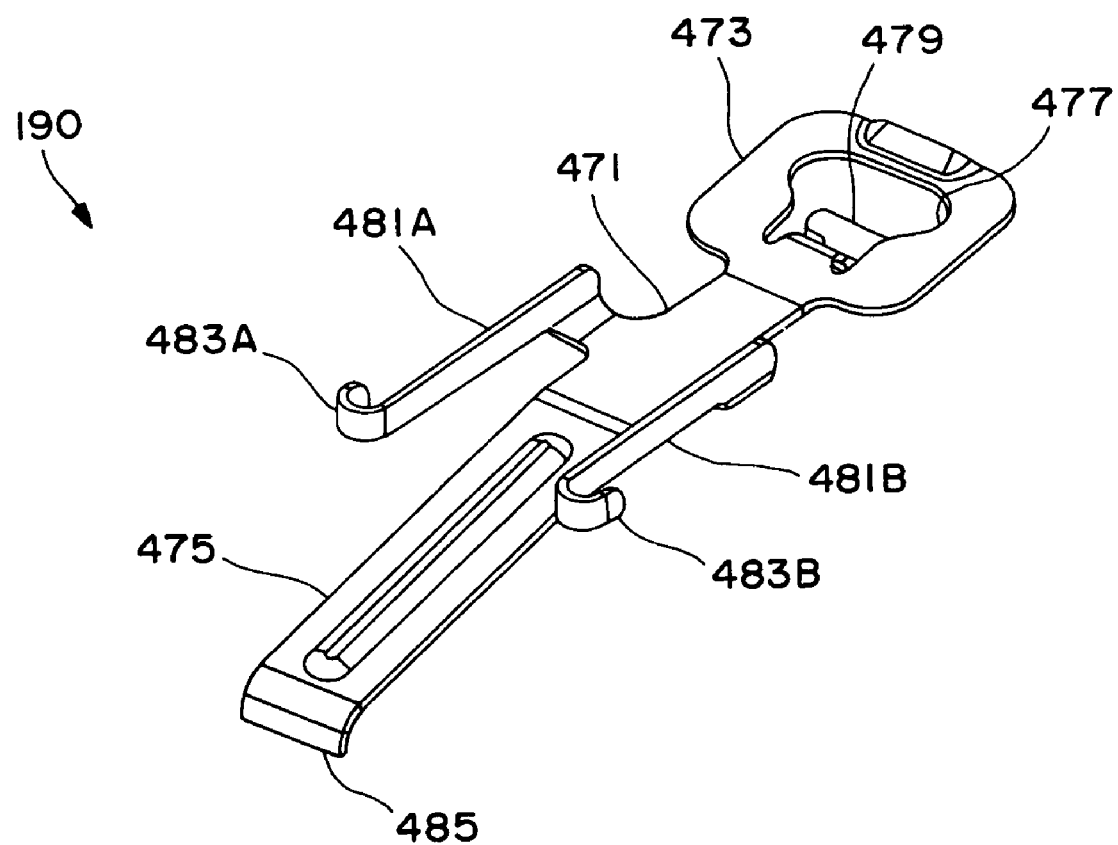
FIG. 12 is a perspective view of an anti-backup spring element provided with the clip applier in accordance with the present invention.
Figure 13:
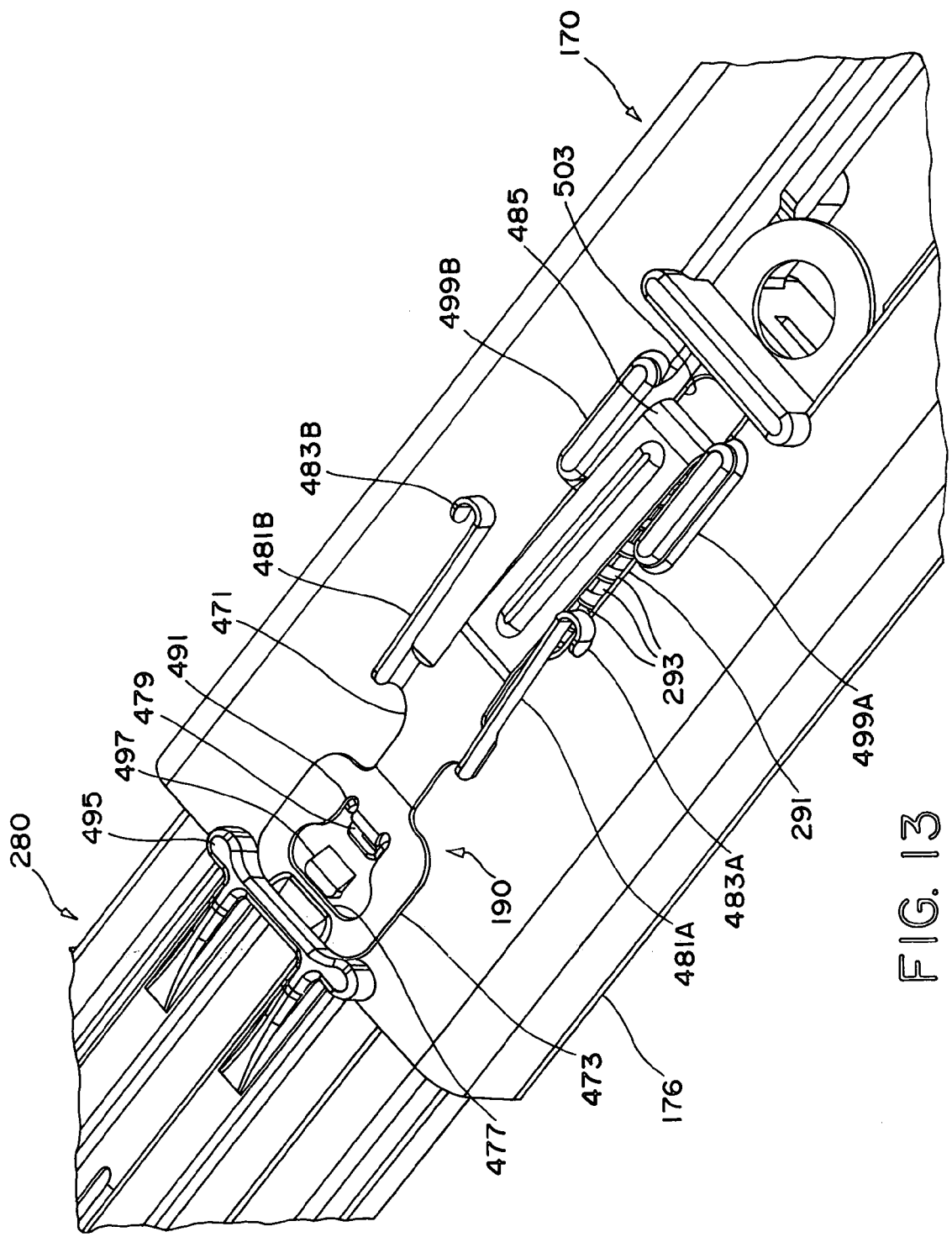
FIG. 13 is a perspective view of the anti-backup spring element illustrated in FIG. 12, wherein the spring element has been mounted to a coupling provided with the clip applier in accordance with the present invention.

Referring now to FIGS. 12 and 13, anti-backup spring element 190 comprises a medial section 471 interposed between a head section 473 and a tail section 475. In the unbiased state of anti-backup spring element 190, medial section 471, head section 473, and tail section 475 each generally lie in different planes and thus are angled away from each other. Head section 473 includes a central opening 477. A mounting tab 479 extends from central opening 477, below the plane of head section 473. Anti-backup spring element 190 also comprises two spring arms 481A and 481B extending from the side edges of medial section 471, on the side of anti-backup spring element 190 opposite to that from which mounting tab 479 and tail section 475 extend. Spring arms 481A and 481B are angled away from the plane of medial section 471. Spring arms 481A and 481B terminate at respective hook-shaped cam followers 483A and 483B, which curve outwardly in relation to the central longitudinal axis of anti-backup spring element 190. Tail section 475 terminates at a pawl 485 that curves away from the main plane of tail section 475.

As illustrated in FIG. 13, in assembling clip applier 100, anti-backup spring element 190 is mounted to the side of box section 176 of coupling 170 opposite to the side visible in FIGS. 3, 5, and 14A–14E (i.e., opposite to the side containing lateral slots 178A and 178B). To assist in properly mounting anti-backup spring element 190 to coupling 170, coupling 170 includes a head mounting slot 491 formed in box section 176 and spring alignment features 495, 497, 499A and 499B extending outwardly from box section 176. Anti-backup spring element 190 is secured to coupling 170 by inserting mounting tab 479 of head section 473 into head mounting slot 491 such that mounting tab 479 abuts an inside surface of the wall of box section 176. At this position, it can be seen from FIG. 13 that a portion of head section 473 is securely retained between two of the spring alignment features 495 and 497 of coupling 170, and lateral movement of tail section 475 is restricted by the other two spring alignment features 499A and 499B. It can also be seen that coupling 170 has a central longitudinal slot 503 to expose ratchet section 291 of channel member 280. When mounted to coupling 170, pawl 485 of tail section 475 extends through this longitudinal slot to engage teeth 293 of ratchet section 291.

The operation of the stroke control system of clip applier 100 during an actuation cycle will now be described with reference to FIGS. 14A–16E. FIGS. 14A–14E illustrate the axial movement of coupling 170 and feed bar 330 in relation to channel member 280 (not shown) and second shroud 115B. It will be noted in FIGS. 14A–14E that tube 260 of channel assembly 250 has been removed for clarity. FIGS. 15A–15E illustrate the axial movement of anti-backup spring element 190 in relation to second shroud 115B, and the interaction between anti-backup spring element 190 with the cam features of second shroud 115B to be described below. It will be noted in FIGS. 15A–15E that coupling 170 and all components of channel assembly 250 have been removed for clarity. FIGS. 16A–16E are cross-sectional views of actuator assembly 110 as illustrated in FIGS. 14A–14E and cut away at lines 16A—16A, 16B—16B, 16C—16C, 16D—16D, and 16E—16E, respectively. FIGS. 16A–16E illustrate the stroke section of the interior of actuator assembly 100 through which coupling 170 and anti-backup spring element 190 reciprocate during the forward and return strokes. The toothed portion of ratchet section 291 extends along a length of the stroke section corresponding to the first stage of the forward stroke. Beyond the last, most distal tooth 293 of ratchet section 291, the remaining untoothed length of the stroke section corresponds to the second stage of the forward stroke. FIGS. 16A–16E also illustrate the interaction between anti-backup spring element 190 with the cam features of second shroud 115B, as well as the interaction between pawl 485 and ratchet section 291.

In general, the stroke control system of the invention is designed to meet three criteria. First, the system must prevent clip applier 100 from resetting until actuator assembly 110 has been completely actuated and a clip loaded into jaw assembly 375 has been compressed to its latched condition. Second, during the first stage of the forward stroke, the system must minimize any partial return stroking of triggers 150A and 150B of actuator assembly 110—and hence any rearward motion of coupling 170 and feed bar 330—in the event that hand pressure on triggers 150A and 150B is released by the user. Third, once a clip has been loaded into jaw assembly 375 at the completion of the first stage of the forward stroke, the system must permit the clip to be partially closed and reopened for purposes of repositioning, etc., before full execution of the second stage of the forward stroke (and, consequently, complete closure and latching of the clip) is intended, and without permitting a total reset of clip applier 100.

Figure 14A:
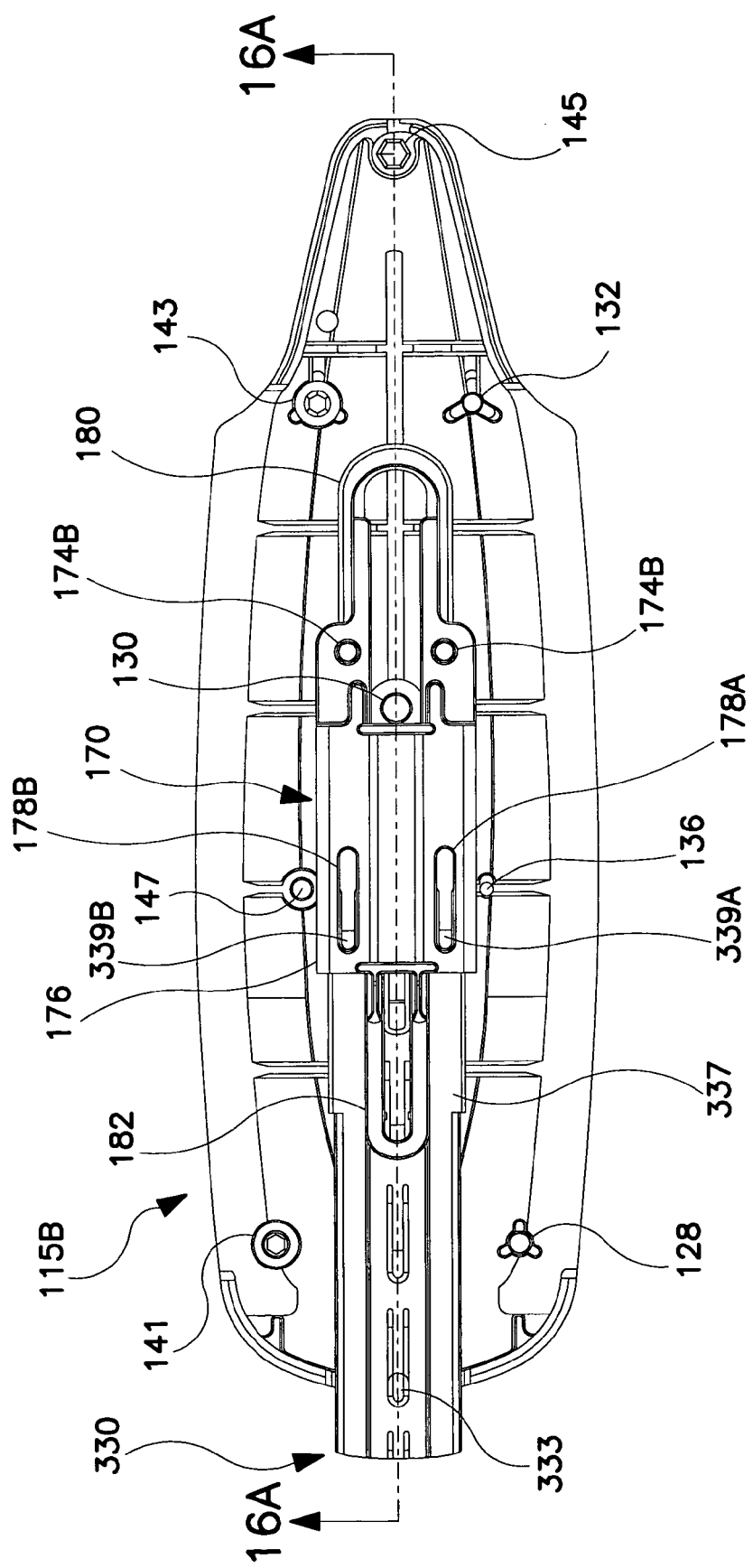
Figure 15B:
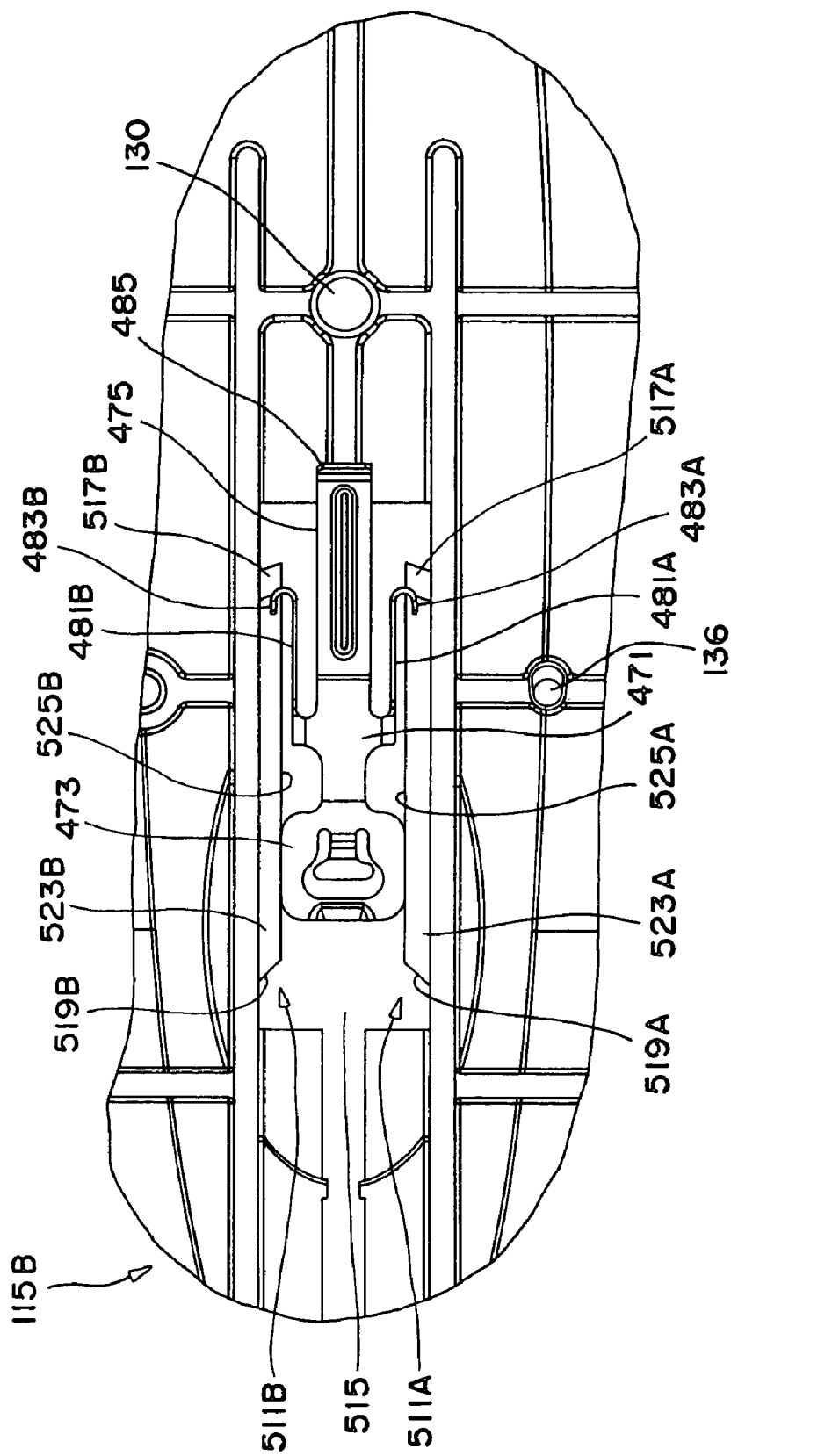
Figure 16A:
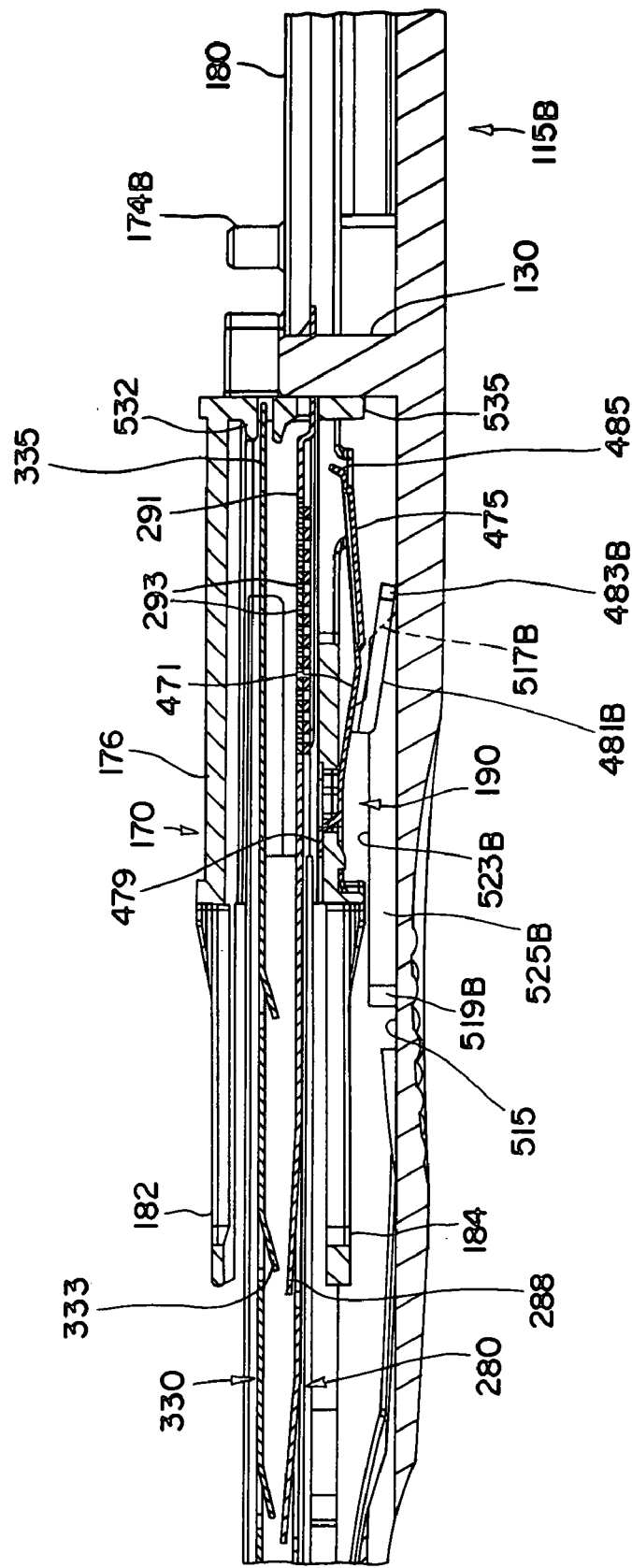
FIGS. 16A–16E are sequential, cutaway side elevation views of a portion of the actuator assembly of the clip applier, illustrating interactions between the coupling, ratchet mechanism, anti-backup spring element, and cam surfaces provided in the actuator assembly.

FIGS. 14A, 15A and 16A illustrate coupling 170 and anti-backup spring element 190 in a rest position, prior to initiation of the forward stroke of actuator assembly 110. As shown in FIG. 14A, coupling 170 is in or near the most proximal position available in relation to second shroud 115B. As shown in FIG. 15A, anti-backup spring element 190 is likewise in or near the most proximal position available in relation to second shroud 115B. In addition, anti-backup spring element 190 is positioned between two parallel, axially oriented cam ribs, generally designated 511A and 511B, formed on an inside planar surface 515 of second shroud 115B. Proximal cam surfaces 517A and 517B are formed at the respective proximal ends of cam ribs 511A and 511B. Proximal cam surfaces 517A and 517B are angled away from inside planar surface 515 in the direction of coupling 170 (not shown in FIG. 15A). Distal cam surfaces 519A and 519B are formed at the respective distal ends of cam ribs 511A and 511B. Distal cam surfaces 519A and 519B are angled toward the central longitudinal axis between cam ribs 511A and 511B in the direction of anti-backup spring element 190. Cam ribs 511A and 511B also provide flat biasing surfaces 523A and 523B that extend between proximal cam surfaces 517A and 517B and distal cam surfaces 519A and 519B. In addition, cam ribs 511A and 511B provide inside lateral surfaces 525A and 525B that extend between proximal cam surfaces 517A and 517B and distal cam surfaces 519A and 519B. Inside lateral surfaces 525A and 525B are perpendicular to biasing surfaces 523A and 523B, and face each other on either side of the central longitudinal axis between cam ribs 511A and 511B.

As further shown in FIGS. 15A and 16A, cam followers 483A and 483B of anti-backup spring element 190 are proximally located in relation to proximal cam surfaces 517A and 517B. As shown in FIG. 16A, cam followers 483A and 483B are in contact with inside planar surface 515 of second shroud 115B. In the rest position shown in FIG. 16A, pawl 485 does not engage any of teeth 293 of ratchet mechanism 291. It can also be seen in FIG. 16A that ratchet section 291 of channel member 280 preferably comprises a series of spaced teeth 293. In one example, there are twelve teeth 293 spaced approximately 1 mm apart from each other. This spacing means that the greatest axial length by which clip applier 100 can be reset during the first stage of the forward stroke is likewise approximately 1 mm. Thus, the presence of and spacing between teeth 293, and the incremental engagement of pawl 485 with teeth 293, assists in meeting the second criterion set forth above (see FIG. 16B).

As additionally shown in FIG. 16A by way of cross-section, a hollow cone 532 is formed in the interior of box section 176 of coupling 170, and extends forwardly from a proximal end wall 535 of box section 176. In assembling clip applier 100, the proximal end of feed bar 330 is inserted into box section 176. As a result, proximal feed bar tabs 339A and 339B deflect into engagement with lateral slots 178A and 178B of box section 176 (see, e.g., FIG. 14A) and axial extension 335 of feed bar 330 is inserted within cone 532. During the operation of clip applier 100, axial extension 335 is coaxially retained by cone 532. However, axial extension 335 is free to move backwardly through cone 532 and out from proximal end wall 535 of box section 176, which will occur during the second stage of the forward stroke as coupling 170 moves forwardly in relation to feed bar 330. Although not shown in FIG. 16A for clarity, feed bar spring 342 (see FIG. 3) is coaxially mounted around axial extension 335 and is compressed between cone 532 and a proximal edge of wide wall section 337 of feed bar 330. Thus, feed bar 330 is not directly affixed to coupling 170, but rather moves forwardly with coupling 170 due the forward biasing force imparted by feed bar spring 342. That is, during forward movement of coupling 170, cone 532 pushes feed bar spring 342 and in response feed bar spring 342 pushes feed bar 330.

Figure 16B:
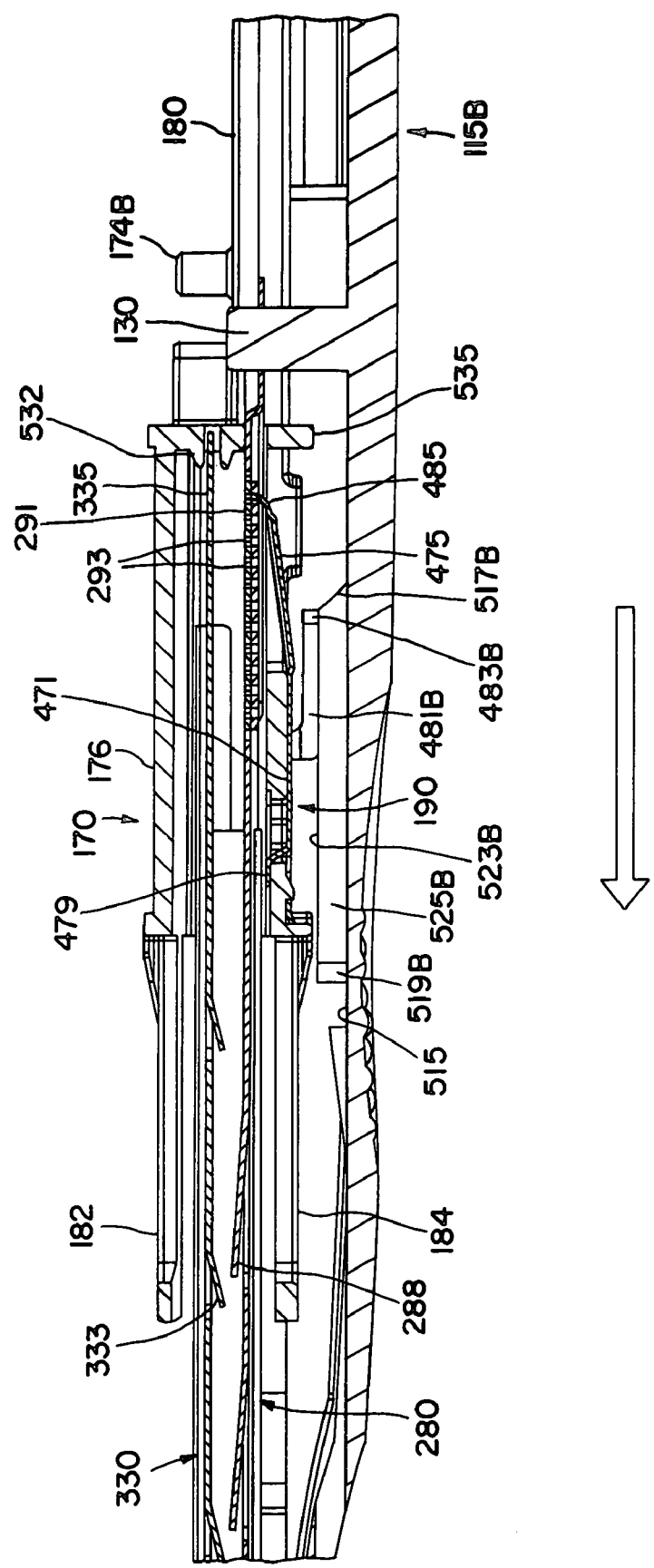

FIGS. 14B, 15B and 16B illustrate the initiation of the first stage of the forward stroke. As shown in FIG. 14B, coupling 170, anti-backup spring element 190, and feed bar 330 have begun to move forwardly. As shown in FIGS. 15B and 16B, this forward movement has forced cam followers 483A and 483B of anti-backup spring element 190 to ride up proximal cam surfaces 517A and 517B and onto biasing surfaces 523A and 523B, thereby causing spring arms 481A and 481B, medial section 471, and tail section 475 to deflect. The deflection of tail section 475 has also caused pawl 485 to contact ratchet section 291 and into engagement with the first adjacent pair of teeth 293. Due to the positional relationship among the various components illustrated in FIG. 16B, pawl 485 is able to engage ratchet section 291 with minimal linear travel. As a result, clip applier 100 becomes locked before the clips CL stored in channel assembly 250 are moved. If, at this point, first and second triggers 150A and 150B were released, clip applier 100 would not be reset because pawl 485 is locked into ratchet section 291. After this point, upon further actuation of the first stage of the forward stroke, cam followers 483A and 483B ride along respective biasing surfaces 523A and 523B of cam ribs 511A and 511B and pawl 485 sequentially moves into engagement between successive pairs of teeth 293. As best shown in FIG. 14C, each tooth 293 is preferably angled in the distal direction to facilitate the incremental, distal movement of pawl 485 along the toothed portion of ratchet section 291, while restricting excessive movement back in the proximal direction. During actuation of the first stage, the most distal clip stored in channel assembly 250 will be loaded into jaw assembly 375 (see the description above relating to FIGS. 11A–11E). If, at any point during actuation of the first stage, first and second triggers 150A and 150B are released, clip applier 100 still cannot be reset because pawl 485 engages at least one tooth 293 along the length of ratchet section 291.

Figure 15C:
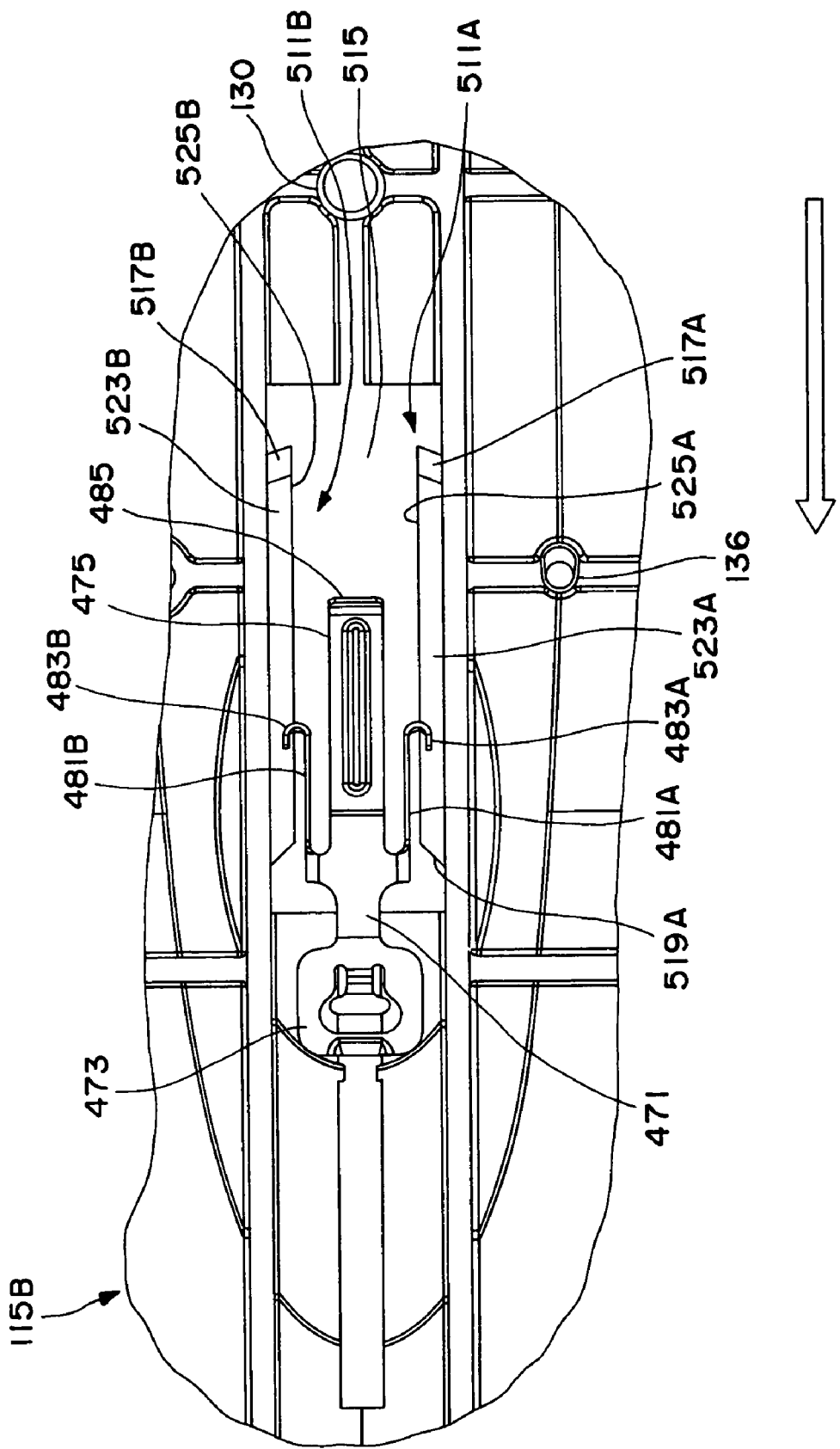
Figure 16C:
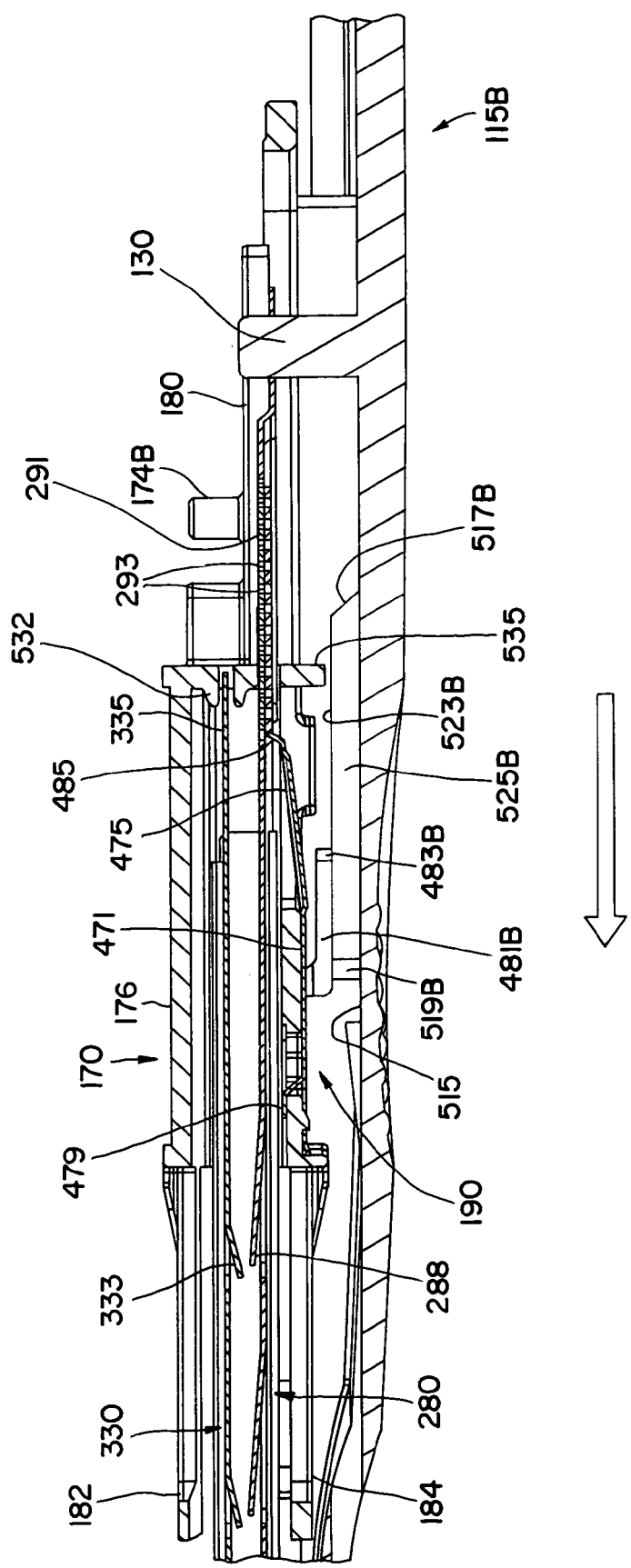

Referring to FIGS. 14C, 15C and 16C, anti-backup spring element 190 has been sufficiently advanced forwardly that pawl 485 engages the last, most distal tooth 293 of ratchet section 291. This position roughly corresponds to the completion of the first stage of the forward stroke, and thus the time when the most distal clip has been fully loaded into jaw assembly 375. At this position, anti-backup spring element 190 remains biased by the contact of cam followers 483A and 483B with biasing surfaces 523A and 523B of cam ribs 511A and 511B. However, the tooth pattern provided by ratchet section 291 has ended. Accordingly, the user of clip applier 100 can now execute partial forward and return strokes repeatedly as desired to manipulate and reposition the clip CL loaded in jaw assembly 375. Resetting of clip applier 100 is still prevented because rearward axial translation of coupling 170 and anti-backup spring element 190 will result in pawl 485 again encountering the most distal tooth 293 of ratchet section 291.

Figure 14D:
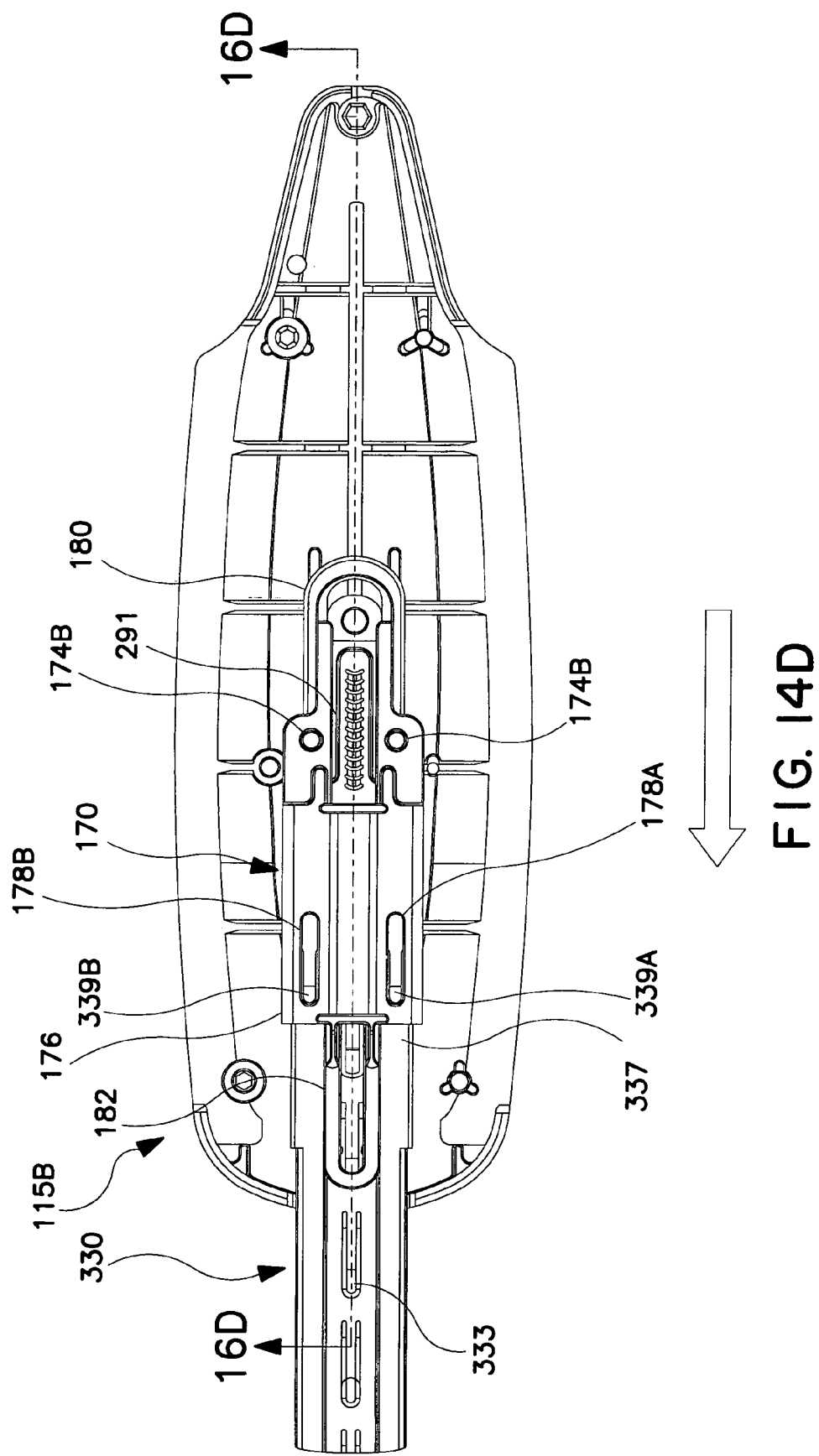
Figure 16D:
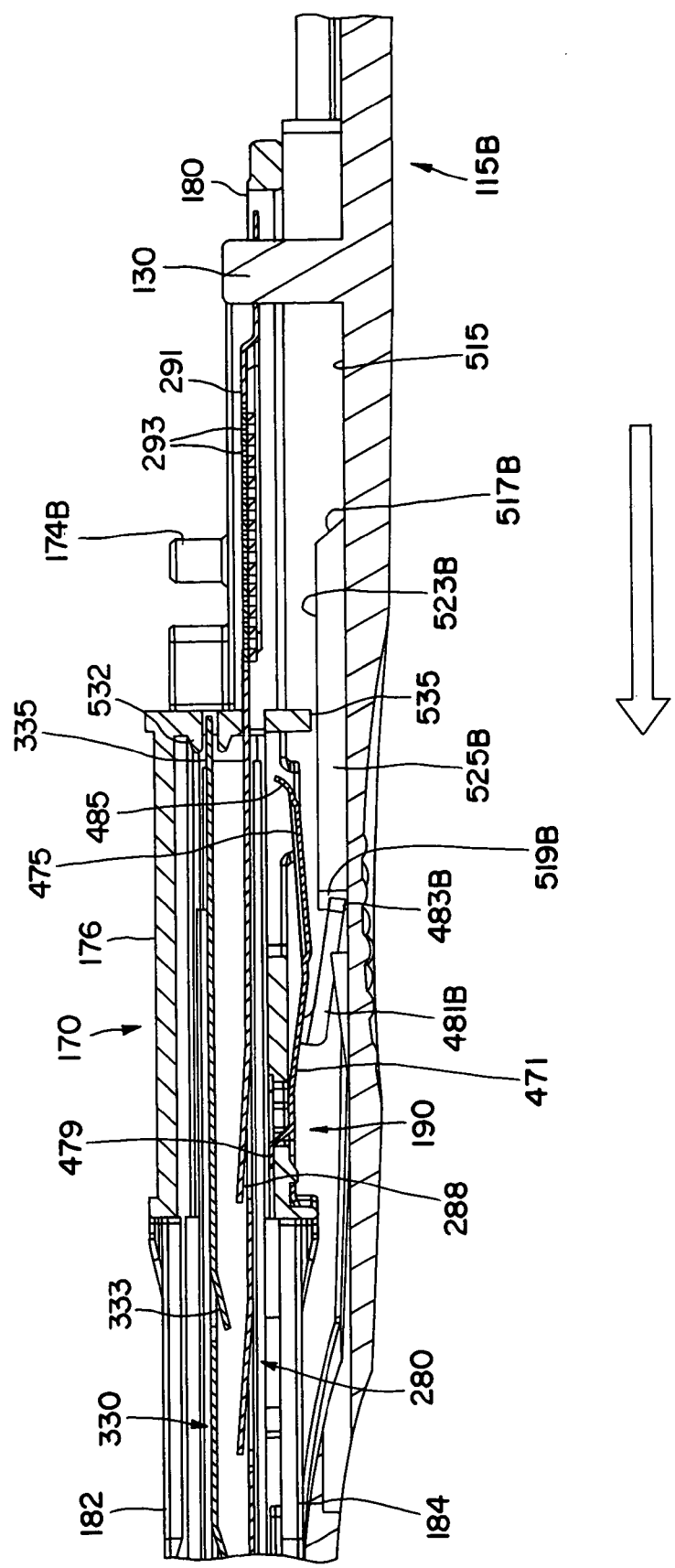

Referring to FIGS. 14D, 15D and 16D, as a result of further actuation of triggers 150A and 150B through the second stage of the forward stroke, anti-backup spring element 190 has been sufficiently advanced forwardly that cam followers 483A and 483B have passed the distal ends of biasing surfaces 523A and 523B and have moved into a relaxed state near or in slightly biased contact with distal cam surfaces 519A and 519B. Preferably, this position corresponds as closely as possible to the instance in time just prior to complete latching of the clip CL to the target tissue. Because cam followers 483A and 483B are no longer biased by biasing surfaces 523A and 523B, spring arms 481A and 481B, medial section 471, tail section 475, and pawl 485 have deflected back to their unbiased states. This enables the ensuing return stroke and hence the resetting of actuator assembly 110 to be accomplished because, as shown in FIG. 16D, clearance now exists between pawl 485 and ratchet section 291. That rearward translation of anti-backup spring element 190 during the return stroke will not result in pawl 485 becoming engaged with any teeth 293.

Figure 14E:
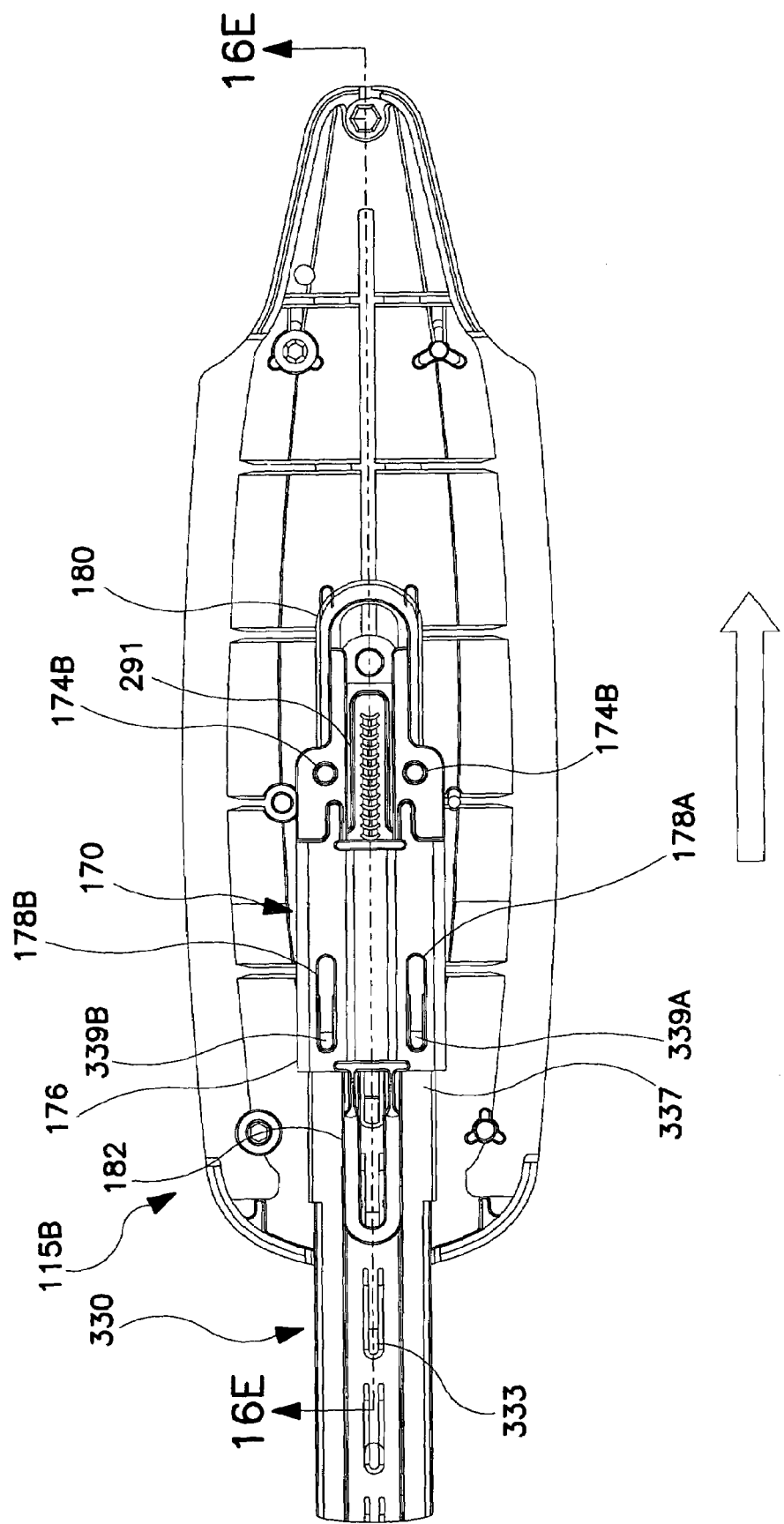
Figure 15E:
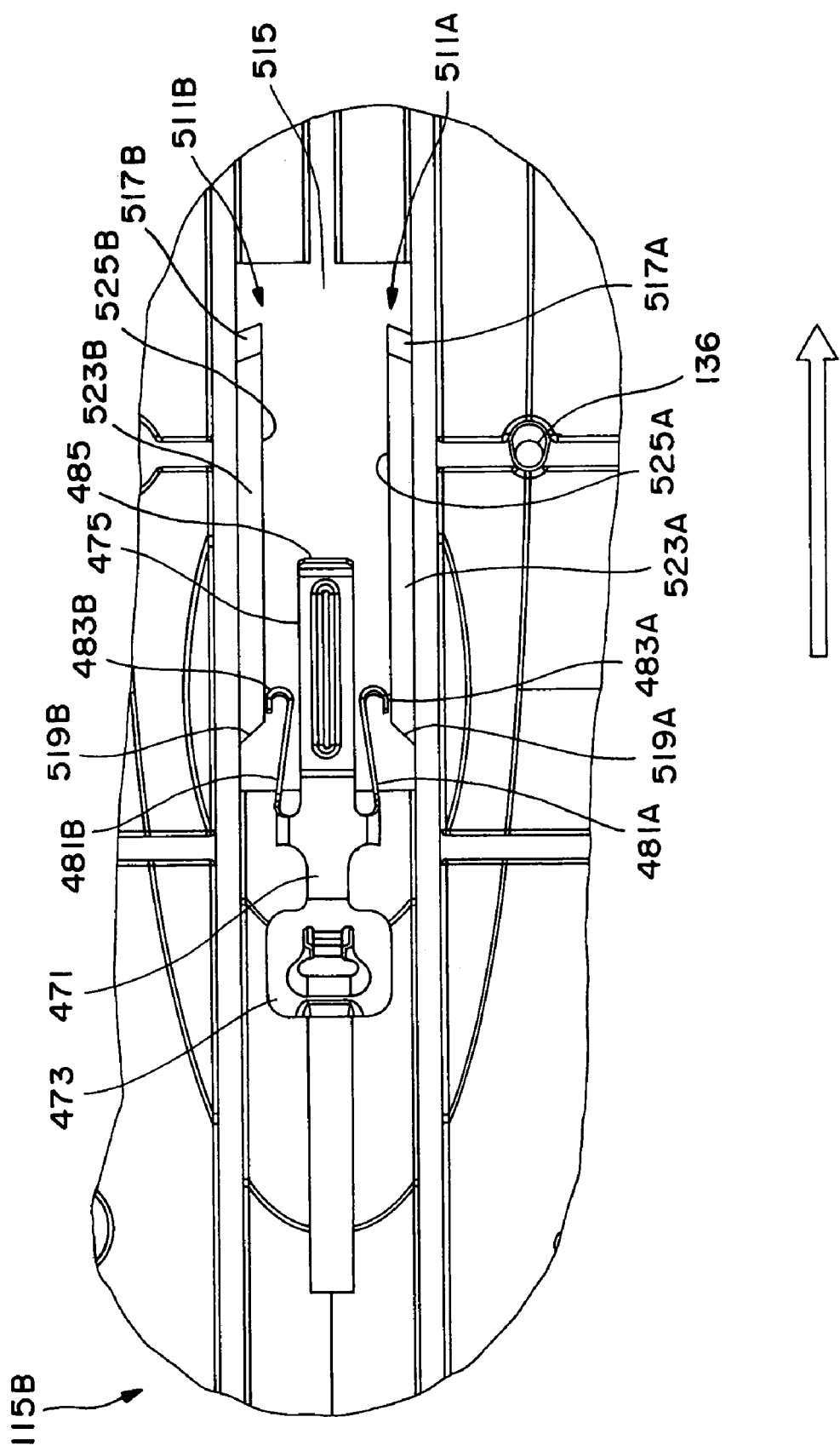
Figure 16E:
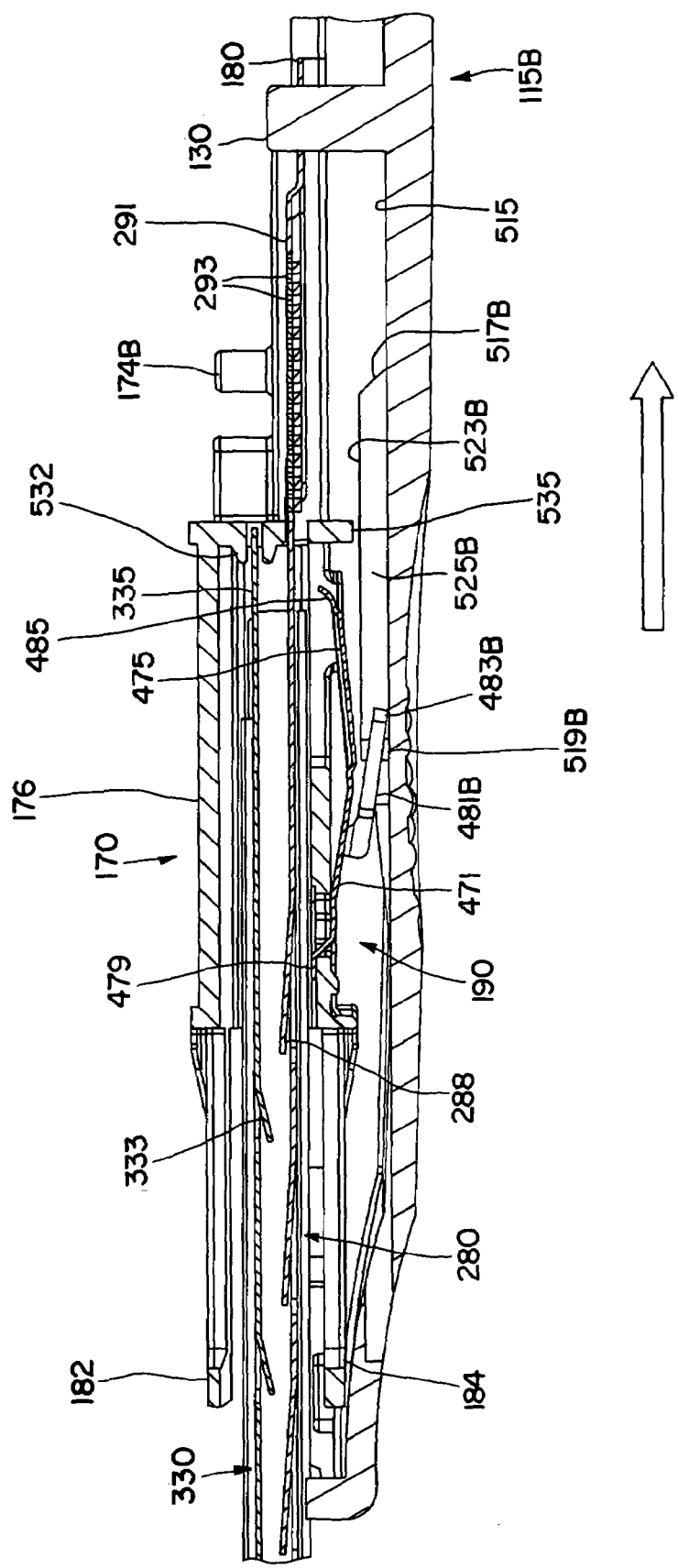

FIGS. 14E, 15E, and 16E illustrate the positions of coupling 170, feed bar 330 and anti-backup spring element 190 during the return stroke. As best shown in FIG. 15E, to ensure that anti-backup spring element 190 remains in its unbiased state so that pawl 485 does not move into locking engagement with ratchet section 291, distal cam surfaces 519A and 519B have forced cam followers 483A and 483B to deflect inwardly towards each other and ride along inside lateral surfaces 525A and 525B of cam ribs 511A and 511B. The biasing of cam followers 483A and 483B against respective inside lateral surfaces 525A and 525B prevents cam followers 483A and 483B from deflecting back toward coupling 170 and ratchet section 291, which would cause pawl 485 to deflect into engagement with ratchet section 291. At the end of the return stroke, and thus the completion of one clip application cycle, the stroke control system just described returns to the resting state illustrated in FIGS. 14A, 15A, and 16A. At the end of the cycle, cam followers 483A and 483B pass inside lateral surfaces 525A and 525B and flex back to their original positions adjacent to proximal cam surfaces 517A and 517B, and the system is ready for the next actuation cycle.

It will be understood that various details of the invention may be changed without departing from the scope of the invention. Furthermore, the foregoing description is for the purpose of illustration only, and not for the purpose of limitation—the invention being defined by the claims.

What is claimed is:

1. An apparatus for applying surgical clips, each clip having first and second legs having respective distal end portions, comprising:
   (a) an actuator device;
   (b) first and second opposing jaw members communicating with the actuator device and movable to a closed position from an open position in response to actuation by the actuator device;
   (c) an elongate assembly comprising a proximal end attached to the actuator device and an opposing distal end, the elongate assembly adapted for containing a serial arrangement of clips between the proximal and distal ends;
   (d) a clip driving device disposed in the elongate assembly and communicating with the actuator device, and adapted for sequentially driving clips through the elongate assembly into engagement with the first and second jaw members in response to actuation by the actuator device; and
   (e) a clip pivot surface disposed in the elongate assembly at its distal end for contacting the distal end portion of the first leg a clip to cause the clip to rotate about the distal end portion of the second leg of the clip in a plane spanning both legs of the clip prior to the clip being driven into engagement with the first and second jaw members.

2. The apparatus according to claim 1 wherein the actuator device comprises an axially translatable coupling attached in actuating engagement with the clip driving device.

3. The apparatus according to claim 2 wherein the actuator device comprises first and second opposing triggers pivotable toward each other from the open position to the closed position, the first and second triggers communicating with the coupling through a linkage mechanism for translating pivoting motion of the first and second triggers into axial motion of the coupling.

4. The apparatus according to claim 2 wherein the elongate assembly comprises a rod disposed distally in relation to the coupling and actuatable by the coupling into contact with the first and second jaw members to cause the first and second jaw members to move to the closed position.

5. The apparatus according to claim 4 wherein the rod is a hollow tubecircumscribing the clip driving device.

6. The apparatus according to claim 1 wherein the elongate assembly comprises a rod communicating with the actuator device and actuatable by the actuator device into contact with the first and second jaw members to cause the first and second jaw members to move to the closed position.

7. The apparatus according to claim 1 comprising a clip saddle surface disposed in the elongate assembly at its distal end for engaging a second end of the clip prior to being driven into engagement with the first and second jaw members.

8. The apparatus according to claim 7 comprising a clip control element disposed in the elongate assembly, wherein the clip control element comprises first and second resilient legs, the first leg comprises the clip pivot surface, and the second leg comprises the clip saddle surface.

9. The apparatus according to claim 8 wherein the elongate assembly comprises a channel member for guiding a clip toward the distal end, the clip driving device moves in relation to the channel member, and the clip control element is attached to the channel member.

10. The apparatus according to claim 7 comprising a clip retainer surface disposed in the elongate assembly, the clip retainer surface adapted to contact the clip while the clip pivot surface contacts the first clip end and the clip saddle surface engages the second clip end.

11. The apparatus according to claim 10 wherein the elongate assembly comprises a channel member for guiding a clip toward the distal end, the clip driving device moves in relation to the channel member, and the clip retainer surface extends from the channel member.

12. The apparatus according to claim 11 wherein the clip pivot surface and the clip saddle surfaces are defined on a clip control element attached to the channel member.

13. The apparatus according to claim 1 wherein the elongate assembly comprises a channel member for guiding the serial arrangement of clips toward the proximal end of the elongate assembly, the channel member comprising a base wall extending between the proximal and distal ends, the base wall comprising a first track for guiding a first side of a clip toward the distal end and a second track for guiding a second side of the clip toward the distal end, wherein the first track comprises a main section spaced from the second track by a track distance and a chicane section spaced from the second track at a greater distance than the track distance to define a diverting path for the second side of the clip.

14. The apparatus according to claim 1 wherein the clip driving device comprises a clip driving tab for sequentially driving clips from the elongate assembly into engagement with the first and second jaw members in response to actuation by the actuator device, and a clip rotating tab for rotating a clip while the clip contacts the clip pivot surface.

* * * * *

UNITED STATES PATENT AND TRADEMARK OFFICE
CERTIFICATE OF CORRECTION

PATENT NO. : 7,052,504 B2  Page 1 of 1
APPLICATION NO. : 10/299360
DATED : May 30, 2006
INVENTOR(S) : J. David Hughett It is certified that error appears in the above-identified patent and that said Letters Patent is hereby corrected as shown below:

Title Page Item (73), Assignee
Please replace "Teleflex Incorporated" with --Pilling Weck Incorporated--.

Signed and Sealed this

Twenty-sixth Day of February, 2008

JON W. DUDAS
*Director of the United States Patent and Trademark Office*